United States Patent
Karpf

(10) Patent No.: US 12,102,837 B2
(45) Date of Patent: Oct. 1, 2024

(54) THERAPEUTIC BIOELECTROMAGNETIC FIELDS, PAIN RELIEF DEVICES, AND RELATED METHODS

(71) Applicant: Gary A. Karpf, Malvern, PA (US)

(72) Inventor: Gary A. Karpf, Malvern, PA (US)

(73) Assignee: Gary A. Karpf, Malvern, PA (US)

( * ) Notice: Subject to any disclaimer, the term of this patent is extended or adjusted under 35 U.S.C. 154(b) by 444 days.

(21) Appl. No.: 17/136,089

(22) Filed: Dec. 29, 2020

(65) Prior Publication Data

US 2021/0113849 A1 Apr. 22, 2021

Related U.S. Application Data

(60) Division of application No. 15/724,347, filed on Oct. 4, 2017, now Pat. No. 10,905,894, which is a continuation-in-part of application No. 15/625,040, filed on Jun. 16, 2017, now abandoned, which is a division of application No. 14/211,579, filed on Mar. 14, 2014, now abandoned.

(60) Provisional application No. 61/799,205, filed on Mar. 15, 2013.

(51) Int. Cl.
*A61N 2/02* (2006.01)
*A61N 1/36* (2006.01)
*A61N 1/40* (2006.01)
*A61N 2/00* (2006.01)

(52) U.S. Cl.
CPC .......... *A61N 2/02* (2013.01); *A61N 1/36021* (2013.01); *A61N 1/40* (2013.01); *A61N 2/008* (2013.01)

(58) Field of Classification Search
CPC ........ A61N 2/02; A61N 1/36021; A61N 1/40; A61N 2/008

USPC ................................ 600/9–15; 128/897–899
See application file for complete search history.

(56) References Cited

U.S. PATENT DOCUMENTS

| | | | |
|---|---|---|---|
| 3,791,801 | A | 2/1974 | Ariga et al. |
| 3,915,151 | A | 10/1975 | Kraus |
| 4,123,511 | A | 10/1978 | Heintze |
| 4,454,118 | A | 6/1984 | Johnson |
| 4,706,672 | A | 11/1987 | Jones |
| 4,891,394 | A | 1/1990 | Savin |
| 5,144,529 | A | 9/1992 | Takahashi |
| 5,148,862 | A | 9/1992 | Hashiura et al. |
| 5,182,171 | A | 1/1993 | Aoyama et al. |
| 5,224,922 | A | 7/1993 | Kurtz |

(Continued)

FOREIGN PATENT DOCUMENTS

| | | |
|---|---|---|
| CN | 1486726 | 4/2004 |
| DE | 1947222 | 4/1971 |

(Continued)

OTHER PUBLICATIONS

English Translation of RU2385169, Mar. 27, 2010, Razumov et al., 13 pages.

(Continued)

*Primary Examiner* — Sunita Reddy
(74) *Attorney, Agent, or Firm* — John F. A. Earley, III; Harding, Earley, Follmer & Frailey, P.C.

(57) ABSTRACT

A pain relief device is provided. The pain relief device includes: (i) a body portion including a contact region configured for contacting a subject; and (ii) a monopolar transmitter including a single electrical pole for providing an electrical signal to the body portion for treatment of the subject.

10 Claims, 12 Drawing Sheets

(56) References Cited

U.S. PATENT DOCUMENTS

| | | | |
|---|---|---|---|
| 6,017,553 | A | 1/2000 | Burrell et al. |
| 6,171,606 | B1 | 1/2001 | Lyons |
| 6,264,681 | B1 | 7/2001 | Usui |
| 6,506,403 | B1 | 1/2003 | Yu |
| 2004/0135997 | A1 | 7/2004 | Chan et al. |
| 2004/0210289 | A1 | 10/2004 | Wang et al. |
| 2005/0107870 | A1 | 5/2005 | Wang et al. |
| 2007/0019359 | A1* | 1/2007 | Elliott .............. A61N 1/14 361/232 |
| 2007/0123952 | A1 | 5/2007 | Strother et al. |
| 2007/0293910 | A1 | 12/2007 | Strother et al. |
| 2008/0207984 | A1 | 8/2008 | Alekseyenko et al. |
| 2008/0294211 | A1* | 11/2008 | Moffitt .............. A61N 1/36146 607/9 |
| 2010/0179373 | A1 | 7/2010 | Pille et al. |
| 2011/0117179 | A1 | 5/2011 | Karpf |
| 2011/0207989 | A1 | 8/2011 | Pilla et al. |
| 2012/0220814 | A1 | 8/2012 | Young |
| 2012/0226095 | A1 | 9/2012 | Young |
| 2013/0123666 | A1 | 5/2013 | Giuffruda et al. |
| 2014/0142654 | A1 | 5/2014 | Simon et al. |
| 2014/0275717 | A1 | 9/2014 | Karpf |
| 2015/0335288 | A1 | 11/2015 | Toth et al. |
| 2016/0106994 | A1 | 4/2016 | Crosby et al. |
| 2017/0086912 | A1 | 3/2017 | Wiener et al. |
| 2017/0189096 | A1 | 7/2017 | Danziger et al. |
| 2020/0000355 | A1 | 1/2020 | Khair |

FOREIGN PATENT DOCUMENTS

| | | |
|---|---|---|
| EP | 0928611 | 7/1999 |
| GB | 3711 | 9/1907 |
| GB | 309394 | 4/1929 |
| GB | 981372 | 1/1965 |
| GB | 2307862 | 6/1997 |
| JP | 58-222011 | 12/1983 |
| JP | 02-275823 | 11/1990 |
| JP | 04-002365 | 1/1992 |
| JP | 06-009363 | 1/1994 |
| JP | 07-016301 | 1/1995 |
| JP | 07-059867 | 3/1995 |
| JP | 2003-137731 | 5/2003 |
| JP | 2004-035440 | 2/2004 |
| RU | 2123329 | 12/1998 |
| RU | 2385169 | 3/2010 |
| WO | 97/20549 | 6/1977 |
| WO | 01/47502 | 7/2001 |
| WO | 2005/023206 | 3/2005 |
| WO | 2005/023213 | 3/2005 |
| WO | 2005/023361 | 3/2005 |
| WO | 2006/133134 | 12/2006 |

OTHER PUBLICATIONS

International Search Report and Written Opinion in counterpart application PCT/US2014/027748 dated Aug. 19, 2014.

International Search Report and Written Opinion mailed Feb. 12, 2019 by the European Patent Office for counterpart international patent application No. PCT/US2018/054190.

Physiomed's LymphaVision, Mar. 8, 2010, 5 pages.

Seoane, F., et al., "Brain Electrical Impedance at Various Frequencies: The Effect of Hypoxia", Proceedings of the 26th Annual International Conference of the IEEE EMBS, Sep. 2004, pp. 2322-2325.

\* cited by examiner

THERAPEUTIC BIOELECTROMAGNETIC FIELDS, PAIN RELIEF DEVICES, AND RELATED METHODS

CROSS-REFERENCE TO RELATED APPLICATIONS

This application is a divisional of U.S. patent application Ser. No. 15/724,347 filed Oct. 4, 2017, which is a continuation-in-part of U.S. patent application Ser. No. 15/625,040 filed Jun. 16, 2017, now abandoned, which is a divisional application of U.S. patent application Ser. No. 14/211,579, filed on Mar. 14, 2014, now abandoned, which, in turn, claims the benefit of priority under 35 U.S.C. § 119(e) to U.S. Provisional Patent Application No. 61/799,205, filed on Mar. 15, 2013, the contents of each of which are incorporated by reference herein, in their entirety and for all purposes.

FIELD

This invention relates generally to treatments for pain, inflammation, and skin disorders, among other conditions. More particularly, the invention relates to such treatments through exposure of the body to a low frequency, low voltage bioelectromagnetic field, or a bioelectric field, or a biomagnetic field that reduces pain, reduces inflammation, and reduces skin disorders such as acne or eczema. Therapeutic low frequency, low voltage bioelectromagnetic fields, a bioelectric fields, or biomagnetic fields may be used to treat any condition described or exemplified herein.

BACKGROUND

Various publications, including patents, published applications, accession numbers, technical articles and scholarly articles are cited throughout the specification. Each cited publication is incorporated by reference herein, in its entirety and for all purposes. Creams and ointments containing certain metals have been used on humans and other animals as protective materials (e.g., sun creams) and for treating a variety of ailments (e.g., rashes and infections). Metal containing products also have been suggested for treating pain. However, the physical properties of useful compositions and devices have not been evaluated systematically.

SUMMARY

According to an exemplary embodiment of the invention, a pain relief device is provided. The pain relief device includes: (i) a body portion including a contact region configured for contacting a subject; and (ii) a monopolar transmitter including a single electrical pole for providing an electrical signal to the body portion for treatment of the subject.

According to another exemplary embodiment of the invention, a method of treating a subject is provided. The method includes the steps of: (a) applying a body portion of a pain relief device to be in contact with the subject, the pain relief device including a monopolar transmitter including a single electrical pole for providing an electrical signal to the body portion; and (b) transmitting the electrical signal to the subject through the body portion using the monopolar transmitter.

According to yet another exemplary embodiment of the invention, a method of determining a medical treatment for a subject is provided. The method includes the steps of: (a) applying test recipes to a plurality of subjects to obtain test data; (b) analyzing the test data to formulate treatment options for application to a subject; and (c) programming a device to include the treatment options.

According to yet another exemplary embodiment of the invention, a method of applying a treatment to a subject is provided. The method includes the steps of: (a) applying a treatment to a subject based on a selected treatment option using a programmable pain relief device, the programmable pain relief device including a monopolar transmitter including a single electrical pole for providing electrical signals to the subject; (b) analyzing a condition of the subject through measurements taken using the programmable pain relief device; and (c) adjusting the treatment provided by the programmable pain relief device based on the results of step (b).

According to yet another exemplary embodiment of the invention, a method of analyzing one or more subjects is provided. The method includes the steps of: (a) measuring naturally occurring waveforms on a surface of a body of a subject; and (b) analyzing data resulting from the measuring step.

Aspects of the disclosure provide methods, devices, and compositions for generating beneficial electrical fields for treating one or more conditions in subjects (e.g., humans or other animals, for example domestic and/or agricultural animals).

The invention features a method for treating pain, comprising directly contacting a surface of a region of the body of a subject in need of treatment for pain with an electrical device powered by an external power source and having a voltage of from about 0.1 millivolts (mV) to about 1000 mV for a period of time sufficient to treat the pain, wherein the device has one point of conductive attachment to the surface and wherein the device emits an electric field comprising a frequency of from about 0.1 Hz to about 2 Hz, thereby treating the pain.

In some aspects, exposing the subject to the low frequency, low voltage bioelectromagnetic field is accomplished by bringing a device or composition which produces the low frequency, low voltage bioelectromagnetic field in proximity to, or in direct contact with, the subject. The device or composition may have one or more electrical properties selected from the group consisting of conductance, semi-conductance, inductance, resistance and capacitance. Proximity within which the device or composition is brought to the subject is preferably less than about 10 centimeters, for example, within about 1 to about 5 centimeters.

In some aspects, the frequency of the bioelectromagnetic field is from about 1 Hz to about and 10 Hz. For example, the frequency of the bioelectromagnetic field may be from about 2 Hz to about 7.5 Hz, or even from about 0.5 Hz to about 4 Hz. The voltage of the bioelectromagnetic field may be from about 0.1 mV to about 500 mV. For example, the voltage of the bioelectromagnetic field may be from about 0.1 mV to about 250 mV, or even from about 50 mV to about 250 mV. The frequency of the bioelectromagnetic field may be from about 1 Hz to about 10 Hz and the voltage is from about 0.1 mV to about 500 mV. For example, the frequency may be from about 2 Hz to about 7.5 Hz and the voltage is from about 0.1 mV to about 250 mV. The frequency may be from about 0.5 Hz to about 4 Hz and the voltage may be from about 50 mV to about 250 mV.

The device or composition may comprise an external source of power, such as a battery or an AC or DC circuit.

In some aspects, a pain-relieving or inflammation-reducing bioelectromagnetic field, bioelectric field, or biomagnetic field is produced when the body is brought contact with or brought into proximity of the device or composition such that the device or composition induces, interacts with, or otherwise synergizes with one or more of the natural electric fields, electromagnetic fields, or magnetic field produced by the body, thereby establishing the low frequency, low voltage bioelectromagnetic field, a bioelectric field, or biomagnetic field that produces a pain-relieving or inflammation-reducing effect.

The invention also features methods for treating a skin condition. The methods may comprise exposing the skin of a subject to a low frequency, low voltage bioelectromagnetic field comprising a frequency of from about 0.1 Hz to about 20 Hz and a voltage of from about 0.1 millivolts (mV) to about 1000 mV for a period of time sufficient to treat the skin condition. Exposing the skin of the subject to a low frequency, low voltage bioelectromagnetic field may be accomplished by bringing a device or composition which produces the low frequency, low voltage bioelectromagnetic field in proximity to, or in direct contact with the skin of the subject. The device or composition may have one or more electrical properties selected from the group consisting of conductance, semi-conductance, inductance, resistance and capacitance. The subject may be any animal, including a mammal, and more preferably including a human being. In some aspects, the method may further comprise determining whether the device or composition has an electrical frequency response of from about 0.01 to about 20 Hz and an electrical voltage response of from about 0.1 mV to about 1000 mV.

The skin condition may be for example, one or more of the following: psoriasis, acne, dermatitis, eczema, insect bites or stings, disorders causing swelling, itching, or scaling of the skin, allergic reactions of the skin to environmental allergens, blisters, ulcers, burns, hyperkeratotic lesions, or skin cancer such as melanoma. Acne, itching, and eczema are preferred.

In some embodiments of the method of treating a skin condition, the frequency of the bioelectromagnetic field is from about 1 Hz to about and 10 Hz. For example, the frequency of the bioelectromagnetic field may be from about 2 Hz to about 7.5 Hz, or even from about 0.5 Hz to about 4 Hz. In some embodiments of the method of treating a skin condition, the voltage of the bioelectromagnetic field is from about 0.1 mV to about 500 mV. For example, the voltage of the bioelectromagnetic field may be from about 0.1 mV to about 250 mV, or even from about 50 mV to about 250 mV. In some embodiments of the method of treating a skin condition, the frequency of the bioelectromagnetic field is from about 1 Hz to about 10 Hz and the voltage is from about 0.1 mV to about 500 mV. For example, the frequency may be from about 2 Hz to about 7.5 Hz and the voltage is from about 0.1 mV to about 250 mV. Furthermore, the frequency may be from about 0.5 Hz to about 4 Hz and the voltage may be from about 50 mV to about 250 mV. In some embodiments of the method of treating a skin condition, the proximity within which the device or composition is brought to the subject is less than about 10 centimeters, for example, within about 1 to about 5 centimeters.

In some embodiments of the method of treating a skin condition, the device or composition comprises an external source of power, such as a battery or an AC or DC circuit. In some aspects, the device or composition does not comprise an external source of power. In some aspects, a pain-relieving or inflammation-reducing bioelectromagnetic field, bioelectric field, or biomagnetic field is produced when the body is brought contact with or brought into proximity of the device or composition such that the device or composition induces, interacts with, or otherwise synergizes with one or more of the natural electric fields, electromagnetic fields, or magnetic field produced by the body, thereby establishing the low frequency, low voltage bioelectromagnetic field, a bioelectric field, or biomagnetic field that produces a pain-relieving or inflammation-reducing effect.

It has been found that certain conditions in a subject are responsive to exposure to electrical fields having certain properties. In some aspects, a subject can be treated by exposing the surface (e.g., the skin) of the subject to an electrical field (e.g., a low frequency electrical field) in order to relieve pain or discomfort, reduce inflammation, and/or treat other conditions that are responsive to electrical fields as described herein. In some aspects, in addition to skin conditions, one or more symptoms (e.g., inflammation, pain, etc.) in tissue beneath the skin (e.g., muscles, joints, ligaments, etc.) can be treated by exposing the skin of a subject to an electrical field having a frequency of between about 0.1 Hz and about 10 Hz.

Accordingly, devices and compositions that output electrical fields (e.g., low frequency, for example extremely low frequency, electrical fields) below about 10 Hz (e.g., between 0.1 Hz and 10 Hz) can be placed on or near (e.g., within a few centimeters) the skin surface of a subject in order to improve or relieve symptoms of one or more conditions in the subject (e.g., human patient).

In some aspects, devices or compositions may generate a suitable electrical field. For example, a device may include a battery or other power source and one or more electrical components suitable for generating a useful electrical field. However, a device or composition that generates an electrical field without an external power source also can be used. In some aspects, a device or composition may be responsive to external energy sources (e.g., by absorbing energy) and produce a suitable electrical field. In some aspects, a device includes one or more electrical components that are responsive to external energy sources. However, in some aspects, a device includes a composition (e.g., a material) that is responsive to external energy sources. In some aspects, a composition that includes a plurality of elemental metal particles within a matrix of non-metallic material can be used to provide a suitable electrical field. In some aspects, useful devices and/or compositions are responsive to energy (e.g., electrical fields) produced by the body of a subject (e.g., at the surface of a subject). In some aspects, useful compositions and devices are responsive, without an extrinsic power source, to electrical fields having a frequency of between 0.01 and 100 Hertz (Hz), for example between 0.1 and 10 Hz. In some aspects, the optimal frequency response of a composition or device described herein is between 0.01 and 100 Hz, for example between 0.1 Hz and 10 Hz (e.g., around 0.5 Hz, around 1 Hz, around 2.5 Hz, around 5 Hz, around 7.5 Hz, or around 10 Hz).

In some aspects, the voltage response of a device or composition described herein is between 0.1 mVolt (mV) and 5.0 Volts (V), for example between 0.5 mV and 1 V, between 25 mV and 500 mV, or between 50 mV and 100 mV.

In some aspects a composition or device described herein is designed to be placed on or near the skin surface of a subject (e.g., within 1-10 cm, for example on the surface, or adjacent to the surface, or on clothing that is near the surface, for example within around 1, 2, 3, 4, or 5 cm of the body surface) where it can absorb energy and generate an electrical output that is therapeutically useful.

In some aspects, a composition or device can include one or more electrical components that can provide appropriate frequency and/or voltage responses and/or generate electrical fields with appropriate frequencies and/or voltages as described herein. In some aspects, a power source is included (e.g., a battery or other power source). However, a power source is not required. In some aspects, a composition or device can absorb energy (e.g., from the environment, and/or from the body surface of a subject) and emit a suitable electrical field (e.g., a low frequency electrical field). Accordingly, in some aspects, a composition or device can act as an antenna that absorbs energy (e.g., from a low frequency electrical field that the composition or device is exposed to, for example from the body of a subject).

In some aspects, a composition or device is based on the field effects of elemental metal particles within a matrix of non-metallic material (e.g., without requiring a battery or power source for example). Accordingly, in some aspects a composition comprises a plurality of elemental metal particles incorporated into an organic or synthetic non-metallic matrix (e.g., a non-conducting or semi-conducting matrix). In some aspects, the non-metallic matrix is a plastic, rubber, and/or resin material. In some aspects the plastic, rubber, or resin material interacts with the elemental metal particles to produce an appropriate electrical field effect. In some aspects, the resulting product is shaped or molded to fit on a body surface of interest. However, in some aspects the resulting product can be provided as a flexible sheet, patch, or tape, or in any other suitable configuration. Flexible products can be placed on any surface of the body of interest since they can bend to conform to the shape of the body. In some aspects, the sheet, patch, or tape can include at least one or more adhesive zones or layers (for example, at least one side can include a layer adhesive material) to help attach the sheet or patch to the skin of a patient. However, it should be appreciated that adhesive zones or layers are not required.

In some aspects, a low frequency electrical field emitted by a composition or device described herein is useful to treat pain, inflammation, irritation or other conditions described herein on or beneath the skin of a subject (e.g., joint pains or tissue inflammation beneath the skin of a subject). In some aspects, neurological and/or neuromuscular conditions can be treated. These and other conditions are described in more detail herein.

In some aspects, a composition or device is configured to be placed on the surface of the body of a subject at a location where treatment is desired (e.g., above or near a site of pain, injury, inflammation, or other condition to be treated). In some, aspects, a composition is in the form of a cream or ointment that can be applied to the skin of a subject. In some aspects, a composition is enclosed within a container so that the composition is not in direct contact with the skin, but wherein the container can be placed on the skin (e.g., it is either shaped and/or has one or more features such as a belt, strap, hook, adhesive, or other feature that is adapted to help maintain contact between the container and the body surface of a subject). In some aspects, a composition is fixed within an organic or synthetic matrix to form a sheet of material (e.g., a patch or any suitable size or shape) that can be placed on the skin of a subject. In some aspects, a device (for example an electrical device) is shaped or otherwise adapted to be placed and/or maintained on the body surface of a subject. For example, the device may include one or more belts, straps, hooks, adhesives, or other features for attachment to the subject (or for attachment to the clothes of a subject).

In some aspects, aspects of the disclosure relate to methods for determining whether a composition or device has beneficial electrical properties (e.g., whether the composition or device has appropriate electrical outputs and/or frequency response characteristics). In some aspects, aspects of the disclosure relate to methods of using compositions or devices that have been determined to have beneficial electrical properties to treat one or more conditions in a subject.

In some aspects, conditions that can be treated include skin conditions (e.g., psoriasis, acne, dermatitis, eczema, and other inflammatory skin conditions, for example skin conditions or diseases that cause itching, swelling, and/or scaly skin patches), skin cancer or pre-cancerous conditions such as hyperkeratotic lesions, melanomas, etc.), itching or pain associated with an insect bite or an exposure to an allergen or other environmental stimulus that causes an inflammatory response (e.g., a response to skin contact with poison ivy, poison oak, or other plant or animal stimulus that can cause an inflammatory skin response), skin blisters or ulcers, skin burns (e.g., due to sun burns, chemical burns, and/or heat injuries, for example first, second, or third degree burns), or other conditions that cause itching and/or pain.

In some aspects, conditions that can be treated include injuries or wounds (e.g., lacerations, bruising, soft tissue injuries, bone fractures, burns, cuts).

In some aspects, conditions that can be treated include pain or discomfort (e.g., joint pain, neuromuscular pain, and other forms of pain). In some aspects, pain or discomfort are associated with a disease or condition (e.g., cancer, inflammation, tissue degeneration, injuries, fractures, arthritis, rheumatoid arthritis, osteoarthritis, a degenerative etiology of pain, a discogenic disease, etc.). In some aspects, compositions or devices described herein can be used to relieve pain associated with growth (e.g., in children) or associated with tissue degeneration (e.g., associated with aging). In some aspects, compositions or devices described herein can be used to provide analgesic relief for one or more conditions (for example, analgesic relief may be provided for Osgood Schlatter's Disease, Patella-Femeral syndrome, and/or Chondromalacia). In some aspects, compositions or devices described herein can be used to treat recurring pain (e.g., pain associated with menstrual cramps), seasonal pain or inflammation or irritation, or sporadic pain or inflammation or irritation.

In some aspects, compositions or devices described herein can be used to provide relief for pain associated with musculoskeletal injuries and overuse syndromes (e.g., carpel tunnel syndrome).

In some aspects, compositions or devices described herein can be used to provide relief for pain associated with surgery. In some aspects, compositions or devices described herein can be used with implants for joint repair, non-union fracture repair, etc.

In some aspects, compositions or devices described herein can be used to increase flexibility, mobility, agility, and/or overall activity in subjects that have arthritis (e.g., osteoarthritis), suffer from muscular or neuromuscular degeneration, are injured, have undergone surgery, and/or are undergoing physical therapy.

In some aspects, compositions or devices described herein can be used to improve the focus or increase the alertness of a subject. Accordingly, compositions or devices described herein can be used to treat, reduce, or prevent the effects of sleep deprivation. In some aspects, compositions or devices described herein are useful to treat attention deficit disorder (ADD), attention deficit hyperactivity disorder (ADHD) or other conditions associated with reduced attention, overactivity, impulsivity, or a combination thereof. In some aspects, compositions or devices described herein can be used to treat sleep disorders, e.g., to improve sleeping patterns. In some aspects, compositions or devices described herein can be used to treat mood disorders. In some aspects, compositions or devices described herein can be used as sexual enhancement products (e.g., to increase sensation, to increase libido and/or sex drive, and/or to increase arousal and/or arousal potential).

In some aspects, compositions or devices described herein can be used to treat, prevent, or reduce one or more symptoms of a hangover (veisalgia) associated with alcohol-consumption, for example, headache, nausea, vomiting, irritation, tremor, thirst, dryness of mouth, event recall, discomfort, restlessness, impatience, or a combination thereof.

Compositions or devices described herein also can be used to treat one or more of these effects associated with other conditions (non-alcohol related conditions) including vertigo, motion sickness, or other conditions that can cause one or more of these symptoms in a subject.

In some aspects, compositions or devices described herein can be used as antimicrobial elements.

DETAILED DESCRIPTION

Figure 1A:
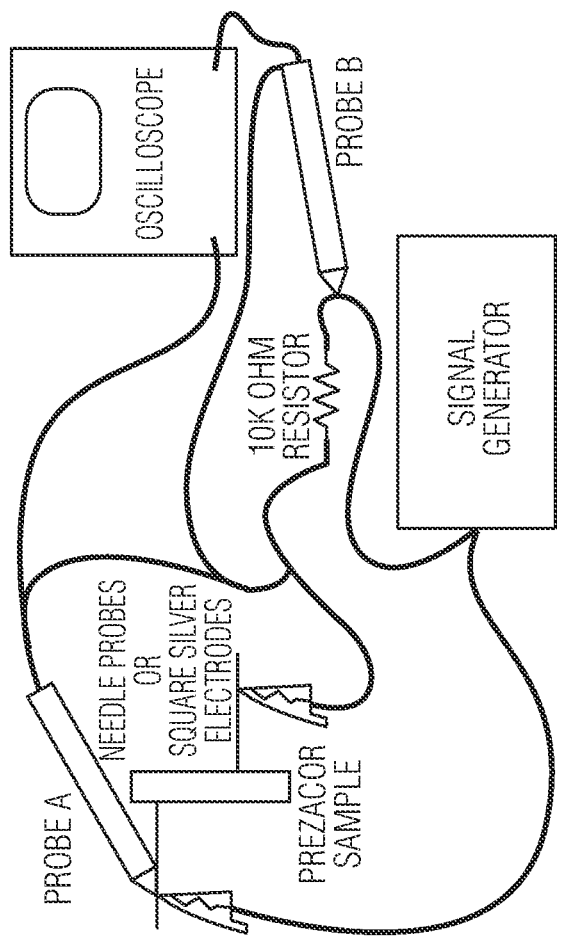
FIGS. 1A-1C illustrate non-limiting examples of circuit configurations that can be used to evaluate the electrical properties of compositions or devices described herein in accordance with various exemplary embodiments of the invention.
Figure 1A:
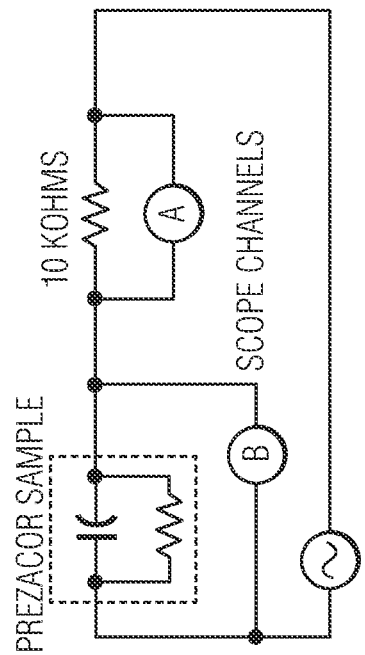

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

In some aspects, aspects of the disclosure relate to methods, compositions, and devices for generating beneficial magnetic, electrical or electromagnetic fields on or near the body of a subject. In some preferred aspects, the generated magnetic, electrical, or electromagnetic fields create, induce, enhance, or synergize with natural magnetic, electrical, and/or electromagnetic fields produced naturally by the body in order to produce a biomagnetic, bioelectric, and/or bioelectromagnetic field that produces a therapeutic effect in the body, including a pain-reducing, inflammation-reducing, and/or healing effect. The biomagnetic, bioelectric, and/or bioelectromagnetic field that is produced preferably has a low frequency and low voltage, and in some aspects preferably has a lower frequency than the magnetic, electrical, and/or electromagnetic fields produced naturally by the body. The biomagnetic, bioelectric, and/or bioelectromagnetic field that is produced may stimulate the parasympathetic nervous system, and may produce a parasympathetic effect.

Devices and compositions suitable for use in the methods of the invention, which are described in detail hereinafter have one or more electrical properties (e.g., conductance and/or semi-conductance, inductance, resistance, capacitance, etc.) that provide beneficial electrical frequency and/or voltage responses and/or outputs when placed on or near the body of a subject. In some aspects, a composition or device has the ability to generate an intrinsic electrical charge, hold an electrical charge, and/or discharge energy spontaneously and/or intrinsically. In some aspects, a composition or device absorbs and then discharges an electrical charge. In some aspects, discharge occurs at a lower frequency than absorption of the electrical charge through conductance and/or the field effect of inductance.

In some aspects, a device or composition provides a therapeutic field effect when it is in physical proximity and/or contact with the surface of a biological living tissue (e.g., the surface of the body of a subject). A subject may be any animal, and preferably is a mammal. Preferred mammals include farm animals (e.g., horses, cows, etc.), laboratory animals (e.g., rabbits, rats, mice), companion animals (e.g., cats, dogs), and non-human primates. Human beings are highly preferred. Whether the device or composition is in direct contact, or in proximity with the subject, as well as the degree of proximity, may depend, for example, on the characteristics of the subject (e.g., age, sex, height, weight, muscle mass), as well as the type and severity of pain or inflammation being experienced by the subject. For example, proximity within which the device or composition is brought to the subject is preferably less than about 10 centimeters, more preferably from about 1 to about 5 centimeters. Proximity may be less than about 1 cm. The device or composition may directly contacted with the a body surface of the subject.

In some aspects, a biologically effective frequency response of a composition or device described herein (e.g., when within physical proximity and/or contact with the surface of biological living tissue) is within the range of 0.01 Hz to 1000.0 Hz, including about 0.01 Hz to about 500 Hz. In some aspects, a low frequency electrical field has a frequency of about 0. 1 Hz to about 25 Hz (e.g., less than about 25 Hz, less than about 20 Hz, less than about 15 Hz, less than about 10 Hz, less than about 8 Hz, less than about 6 Hz, less than about 5 Hz, less than about 4 Hz, less than about 2 Hz, less than about 1 Hz, less than about 0.5 Hz, or less than about 0.2 Hz, or within a frequency range of from about 0.1 Hz to about 25 Hz, from about 0.1 Hz to about 20 Hz, from about 0.2 Hz to about 5 Hz, or from about 0.5 Hz and 6 Hz).

The frequency of the bioelectromagnetic field may be from about 0.1 Hz to about 25 Hz, from about 0.1 Hz to about 20 Hz, from about 0.1 Hz to about 18 Hz, or from about 0.1 Hz to about 15 Hz, or from about 0.1 Hz to about 12 Hz, or from about 0.1 Hz to about 10 Hz, or from about 0.1 Hz to about 8 Hz, or from about 0.1 Hz to about 7.5 Hz, or from about 0.1 Hz to about 6 Hz, or from about 0.1 Hz to about 5 Hz, or from about 0.1 Hz to about 4 Hz, or from about 0.1 Hz to about 3 Hz, from about 0.1 Hz to about 2 Hz. The frequency of the bioelectromagnetic field may be from about 0.5 Hz to about 25 Hz, from about 0.5 Hz to about 20 Hz, from about 1 Hz to about 20 Hz, from about 1 Hz to about 10 Hz, from about 1 Hz to about 8 Hz, from about 1 Hz to about 5 Hz, from about 1 Hz to about 3 Hz, from about 2 Hz to about 16 Hz, from about 2 Hz to about 18 Hz, from about 2 Hz to about 20 Hz, from about 2 Hz to about 14 Hz, from about 2 Hz to about 12 Hz, from about 2 Hz to about 10 Hz, from about 2 Hz to about 8 Hz, from about 2 Hz to about 6 Hz, from about 3 Hz to about 17 Hz, from about 3 Hz to about 15 Hz, from about 3 Hz to about 10 Hz, from about 3 Hz to about 7 Hz, from about 3 Hz to about 6 Hz, from about 4 Hz to about 22 Hz, from about 4 Hz to about 16 Hz, from about 4 Hz to about 12 Hz, from about 4 Hz to about 8 Hz, from about 4 Hz to about 6 Hz, from about 5 Hz to about 20 Hz, from about 5 Hz to about 10 Hz, from about 5 Hz to about 8 Hz, from about 6 Hz to about 10 Hz, from about 6 Hz to about 16 Hz, from about 6 Hz to about 11 Hz, from about 8 Hz to about 20 Hz, from about 8 Hz to about 12 Hz, from about 8 Hz to about 10 Hz, from about 10 Hz to about 20 Hz, from about 0.1 Hz to about 10 Hz, from about 0.5 Hz to about 10 Hz, from about 0.5 Hz to about 18 Hz, from about 0.2 Hz to about 6 Hz, from about 0.3 Hz to about 7 Hz, from about 0.4 Hz to about 6 Hz, from about 5 Hz to about 16 Hz, from about 6 Hz to about 10 Hz, from about 7 Hz to about 10 Hz, from about 8 Hz to about 10 Hz, from about 12 Hz to about 18 Hz, from about 14 Hz to about 25 Hz, from about 15 Hz to about 20 Hz, from about 11 Hz to about 19 Hz, or from about 13 Hz to about 20 Hz.

In some aspects, a biologically effective voltage response of a composition or device described herein (e.g., when within physical proximity and/or contact with the surface of biological living tissue) is within the range of 0.5 mVolt to 5.0 Volts. In some aspects, a useful low frequency electrical field is between 0.5 mV and up to several V, for example between 0.5 mV and 900 mV, between 1 mV and 500 mV, between 25 mV and 500 mV, around 50 mV, around 100 mV, around 250 mV, around 500 mV, around 750 mV, or around 1 V.

The voltage of the bioelectromagnetic field may be from about 0.1 millivolts (mV) to about 1000 mV, or from about 0.1 millivolts (mV) to about 800 mV, or from about 0.1 millivolts (mV) to about 600 mV, or from about 0.1 millivolts (mV) to about 500 mV, or from about 0.1 millivolts (mV) to about 400 mV, or from about 0.1 millivolts (mV) to about 250 mV, or from about 0.1 millivolts (mV) to about 200 mV, or from about 0.1 millivolts (mV) to about 100 mV, or from about 0.1 millivolts (mV) to about 75 mV from about 0.1 millivolts (mV) to about 50 mV, or from about 0.1 millivolts (mV) to about 25 mV, or from about 0.1 millivolts (mV) to about 10 mV. Similarly, without limitation, the voltage of the bioelectromagnetic field may be from about 1 millivolts (mV) to about 1000 mV, or from about 10 millivolts (mV) to about 1000 mV, or from about 50 millivolts (mV) to about 1000 mV, or from about 100 millivolts (mV) to about 1000 mV, or from about 250 millivolts (mV) to about 1000 mV, or from about 500 millivolts (mV) to about 1000 mV, or from about 600 millivolts (mV) to about 1000 mV, or from about 750 millivolts (mV) to about 1000 mV, or from about 800 millivolts (mV) to about 1000 mV. Even more specifically, the without limitation, the voltage of the bioelectromagnetic field may be from about 100 millivolts (mV) to about 750 mV, or from about 250 millivolts (mV) to about 750 mV, or from about 50 millivolts (mV) to about 500 mV, or from about 50 millivolts (mV) to about 250 mV, or from about 10 millivolts (mV) to about 100 mV, or from about 10 millivolts (mV) to about 50 mV, or from about 1 millivolts (mV) to about 100 mV, or from about 1 millivolts (mV) to about 50 mV, or from about 1 millivolts (mV) to about 25 mV.

In some preferred aspects, the frequency of the bioelectromagnetic field is from about 1 Hz to about 20 Hz and the voltage is from about 0.1 mV to about 500 mV. In some preferred aspects, the frequency of the bioelectromagnetic field is from about 2 Hz to about 8 Hz and the voltage is from about 0.1 mV to about 500 mV. In some preferred aspects, the frequency of the bioelectromagnetic field is from about 4 Hz to about 16 Hz and the voltage is from about 0.1 mV to about 500 mV. In some preferred aspects, the frequency of the bioelectromagnetic field is from about 1 Hz to about 10 Hz and the voltage is from about 0.1 mV to about 500 mV. For example, the frequency may be from about 2 Hz to about 7.5 Hz and the voltage is from about 0.1 mV to about 250 mV. Furthermore, the frequency may be from about 0.5 Hz to about 4 Hz and the voltage may be from about 50 mV to about 250 mV.

In some aspects, electrical field effects of a device or composition described herein can be evaluated experimentally. For example, in some aspects a test circuit can be used to determine that the frequency and/or voltage output and/or response of a composition or device described herein are within desirable ranges. In some aspects, one or more non-limiting circuits illustrated in FIG. 1 and/or one or more technique illustrated in the examples can be used to evaluate or measure the frequency or voltage output and response of devices or compositions of interest. However, it should be appreciated that other techniques may be used as aspects of the disclosure are not limited in this respect. Also, in some aspects compositions or devices that have been tested and shown to have appropriate frequency and/or voltage responses can be further evaluated and optimized by testing their effects on physiological conditions (for example on one or more of the conditions described herein). Thus, in some embodiments the methods may optionally include first determining whether the device or composition has an electrical frequency response of from about 0.01 to about 20 Hz and an electrical voltage response of from about 0.1 mV to about 1000 mV, for example, prior to bringing the device or composition into proximity or direct contact with the subject.

Compositions and devices that produce low frequency electrical fields on or near the body surface of a subject are useful to promote healing and/or pain relief in the subject in addition to being effective for other conditions described herein.

Devices and compositions that produce low frequency electrical fields can include batteries or other sources of power, such as an AC or DC circuit. In some aspects, the device or composition does not need to include a power source and instead can generate a suitable low frequency electrical field from absorbed energy (e.g., electromagnetic energy). For example, energy from the body of a subject can be absorbed and emitted in the form of a suitable low frequency electrical field. For example, without intending to be limited to any particular theory or mechanism of action, it is believed that a therapeutic bioelectromagnetic field, bioelectric field, or biomagnetic field may be produced when the body is brought contact with or brought into proximity of the device or composition that induces, interacts with, or otherwise synergizes with one or more of the natural electric fields, electromagnetic fields, or magnetic field produced by the body, thereby establishing the low frequency, low voltage bioelectromagnetic field, a bioelectric field, or biomagnetic field that produces the desired therapeutic effect. In some aspects, a composition comprising a plurality of elemental metal particles dispersed within a non-metallic matrix (e.g., a non-conducting or semi-conducting matrix, for example an organic matrix) can act as an antenna and produce a low frequency electrical field from absorbed electromagnetic energy.

Devices and compositions having properties described herein produce a biological field effect that can be used to treat a range of conditions associated with pain, injury, inflammation, and other conditions that are responsive to an electrical effect as described herein.

Aspects of the invention are based, in part, on the discovery that certain configurations of elemental metals resulting in particular electrical frequency and voltage responses and outputs have surprising effects on many biological processes. In particular, compositions comprising one or more elemental metal structures that are mixed and/or coated with one or more non-conducting and/or semi-conducting materials can have significant therapeutic and/or agricultural uses when placed on or near biological living tissue. In some aspects, certain elemental metal compositions interact with electrical fields (e.g., electrostatic and/or electromagnetic fields) associated with living biological systems (e.g., cells, tissue, organs, organisms, etc.) and this interaction can be used to alter certain biological processes. In contrast to compositions that deliver metal ions for direct chemical interactions with biological processes and molecules, aspects of the present invention provide compositions with electrical properties that impact a living biological tissue indirectly through field effects that do not require direct contact with the biological system. Accordingly, although compositions described herein may be applied to a biological surface (e.g., skin) in the form of a cream or ointment, compositions or devices described herein also may be effective when put in close proximity to a biological surface (e.g., a composition may be provided in an enclosure or container that is placed on or near a biological tissue, or a composition may be provided in the form of a plastic, rubber, or resin sheet or film that can be placed on or near a biological tissue, or a device having suitable electrical properties can be placed on or near a biological tissue).

In some aspects, compositions having useful electrical properties can be based on a plurality of conducting elemental metal particles (e.g., balls, beads, powder, nanoparticles, etc.) that are separated from each other by a matrix of non-metallic material (e.g., non-conducting or semi-conducting material, for example organic material). Electrical properties of these compositions can be assessed as described herein and compositions of interest can be selected based on their electrical properties and/or further tested for their physiological properties.

In some aspects, the separating matrix material can be in the form of solid particles that are mixed with the elemental metal particles (e.g., in the form of a dry mixture). In some aspects, the separating matrix material may be in the form of a coating that can be mixed with or applied to the elemental metal particles. The coating may be mixed or applied in a viscous, liquid, or aerosol form. It should be appreciated that a matrix may include a combination of solid particles and coating(s). The resulting composition may be a dry, viscous, or otherwise flowable composition depending on the intended use. For example, the composition may be a solid, liquid, grainy, semi-solid, waxy, oily, or low viscosity composition comprising elemental metal particles at least some of which are separated from each other by a matrix of non-conducting and/or semi-conducting material.

In some aspects, the separation of the conducting elemental metal particles within a matrix produces certain electrical properties that can interact with living biological systems and alter the nature and/or magnitude (e.g., intensity, speed, etc.) of certain biological processes. It should be appreciated that the nature, dimensions, and relative amounts of the elemental metal and the matrix materials may alter the electrical properties of a composition and may be optimized for a particular biological application.

Accordingly, one aspect of the invention provides a biologically active elemental metal composition including one or more elemental metal particles within a matrix of non-conducting or semi-conducting material wherein the composition has been evaluated to determine that it has useful electrical frequency and/or voltage responses and/or outputs.

In some aspects, the matrix can be a coating material that is disposed around at least a fraction of the surface area of the particulate elemental metal(s). In some aspects, the matrix may be, or may include, a particulate material that is mixed with the elemental metal particles and that separates at least a fraction of the elemental metal particles from each other. For example, the material may be a semi-conducting material. For example, the matrix material can include a silicon dust, sulfur, boron, fiberglass, or other suitable material.

In some aspects, the elemental metal particles are incorporated in (e.g., dispersed within) a non-metallic adhesive matrix, a rubber matrix, a plastic matrix, a colloidal matrix, or a combination thereof. In some aspects, suitable non-metallic matrices can include one or more of the following non-limiting materials: rubber, plastic, resin, silicone (e.g., polymerized siloxanes), expanded polytetrafluoroethylene (PTFE, e.g., available under the name Teflon), vinyl, latex, or one or more other organic polymers, elastomers, or colloidal preparations (e.g., one or more hydrocolloids), or a combination thereof (e.g., a combination of PTFE and silicone, for example available under the name Silon). In some aspects, one or more oils and/or carboxy-methyl cellulose can be used. In some aspects, a composition can be produced in the form of a flexible sheet (e.g., a patch or a tape) that can readily conform to the contours of a body surface region (or other biological surface), for example when it is applied directly to the skin surface of a subject. In some aspects, a sheet can be produced in a size and configuration that can be readily applied to most body surfaces (e.g., above any joints or muscles, on the back, stomach, arm, leg, or forehead, etc.) depending on the condition being treated. In some aspects, at least one side of a sheet of material described herein is sticky (e.g., includes an adhesive layer). In some aspects, a flexible sheet as described herein is made of durable material that is resistant to wear and tear associated with its use on the body surface of a subject. In some aspects, a composition is cured or otherwise processed, for example, to modify its physical properties (e.g., to optimize them for a particular use). In some aspects, a backing may be used to further strengthen a flexible patch or sheet. In some aspects, a polymeric backing may be used (e.g., a thermoplastic polyurethane).

In addition to having desirable electrical and physical properties, it should be appreciated that the elemental metal particles, the non-metallic matrix material, and the adhesive material (if present) can be selected to be physiologically compatible (e.g., non-toxic, non-irritant, stable, and/or water-stable). In some aspects, a composition described herein (for example in any suitable solid form described herein, including for example a solid molded shape and/or a flexible sheet) can be covered with a coating, for example an adhesive coating (e.g., an acrylic adhesive or any other suitable adhesive). In some aspects, a coating covers the entire surface of a composition described herein (e.g., a solid composition), thereby sealing the composition (including, in some aspects, the elemental metal particles and/or the matrix material) within the coating, but still allowing electrical properties of the composition to be effective as described herein.

In some aspects, the disclosure provides a body surface (external) appliance or device constructed to fit a certain body part and containing a compound that is specifically formulated to consist of microscopic capacitors that respond to and resonate with naturally occurring electrical fields (e.g., fields produced by muscle, nerve and/or other body tissue).

Aspects of the disclosure include using one or more compositions or devices described herein to impact one or more biological processes. A composition or device may be used in an amount and for a time sufficient to obtain a particular biological outcome. Biological applications include medical, veterinary, and agricultural applications as described herein. It should be appreciated that different amounts and or exposure times may be appropriate for different applications. Effective and/or optimal compositions and exposure conditions (including amount and/or time of exposure) may be determined for any particular application based on the description and examples provided herein.

In some aspects, compositions or devices are placed on or near the body of a subject for several hours to several days, weeks, or months (e.g., 6-8 hours per day for up to several weeks, for example up to 12-16 weeks or longer, or for 24 hours/day daily, or for a time period that is sufficient to produce a desired effect). In some aspects, a composition or device can be used (for example, used at night, or worn during the day, or both) for an amount of time that is required to treat a particular condition. In some aspects, compositions or devices are used repeatedly or continuously (for several months or even years) to treat a chronic condition. However, in some aspects, compositions or devices are used only when needed.

Accordingly, aspects of the disclosure include non-invasive methods, compositions, and devices, for reducing the severity of pain/inflammation/irritation, delaying the onset of pain/inflammation/irritation, reducing the duration of pain/inflammation/irritation, maintaining or increasing mobility, reducing or preventing the use of topical creams or other medication (e.g., pain killers, anti-inflammatory medications, etc., or any combination thereof), increasing the quality of life (e.g., activity and/or mobility) of a patient, and/or delaying or postponing an invasive surgical procedure (e.g., for pain remediation). However, devices and compositions described herein also may be used for other applications.

In some aspects, metal containing compositions can be evaluated as described herein. Aspects of the invention are based, in part, on the discovery that certain compositions including one or more elemental metals can produce electrical fields that can alter biological processes. In some aspects, biologically active compositions including one or more elemental metals are referred to herein as elemental metal compositions. In certain aspects, the elemental metal(s) are provided in particulate form. In certain aspects, the elemental metal(s) may be coated with one or more non-metallic materials (e.g., non-conducting or semi-conducting materials, for example organic material). In some aspects, elemental metal compositions act as capacitors. In some aspects, elemental metal compositions produce an electrical field (e.g., a low frequency electrical field) that is biologically effective. In some aspects, elemental metal compositions stabilize a biological process when exposed to a biological tissue (e.g., through surface exposure). In some aspects, elemental metal compositions alter a biological process when exposed to a biological tissue (e.g., through surface exposure).

In some aspects, elemental metal particles are contained within a matrix such that the particles (or a fraction thereof) are separated from each other by the matrix material. In one aspect, the matrix includes one or more non-metallic coating materials (e.g., materials that can form a coating or film on the surface of the elemental metal particles) to enhance the biological effects of the composition. In another aspect, the matrix includes one or more particulate materials (e.g., powders, grains, etc.) that can be mixed with the elemental metals to enhance the biological effects of the composition. A coating and/or particulate matrix material may be less conducting than an elemental metal particle (e.g., a matrix coating or particle may be non-conducting or semi-conducting). Accordingly, a composition of the invention may have non-uniform conductivity that contributes to its capacitor and/or field effect properties. The size of the elemental metal particles may affect the capacitor and/or field effect properties of a biologically effective composition. The average distance between elemental metal particles in the composition also may affect the capacitor and/or field effect properties of a biologically effective composition. In one embodiment, a composition containing smaller elemental metal particles has a greater area of surface contact between the elemental metal(s) and the matrix material(s) resulting in stronger capacitor and/or field effects. It should be appreciated that the capacitor and/or field effects of an elemental metal composition also may be affected by the type of elemental metal(s) and matrix material(s) that are used. In addition, the presence of moisture and/or oxidized metals also may affect (e.g., reduce) the capacitor and/or field effects. Accordingly, a matrix material (e.g., coating) also may be used to exclude moisture (e.g., water) and/or protect the elemental metal(s) from oxidation.

Compositions of the disclosure can be used to impact physiological processes in animals (e.g., humans) and/or plants. Accordingly, compositions including elemental metals may be used for therapeutic purposes to treat certain conditions in humans and/or other animals. In other aspects, compositions including elemental metals may be used for agricultural purposes to promote or stabilize certain physiological states in plants.

In one aspect, compositions of the invention may be provided in the form of a topical preparation that can be applied to or contacted to a biological surface (e.g., skin of an animal or surface of a plant). In certain aspects, compositions of the invention may be provided in a container that is adapted to be exposed or contacted to a biological surface (e.g., without the surface being directly contacted by the elemental metal composition). In one embodiment, the elemental metal composition may be formed (e.g., molded) into a solid device having a defined shape (e.g., a shape adapted for contact with a biological surface). In another embodiment, one or more elemental metal(s) may be provided in particulate form and contained within a device (e.g., a shaped device). For example, the elemental metal(s) may be provided in a matrix or in a container/sheath. In one embodiment, the elemental metal(s) may form a single solid structure. In another embodiment, the elemental metal(s) may be in the form of two or more structures having similar or different shapes. In one embodiment, the elemental metal(s) are particulate (e.g., balls, filings, grains, granules, nanoparticles, etc.). The particles all may be of approximately the same size. Alternatively, the particles may range in size. The average size of an elemental metal particles may be smaller or larger than the average size of a matrix particle (e.g., the ratio of elemental metal to matrix particle may be between 1/100 and 100/1, for example between 1/10 and 10/1). However, higher, lower, or intermediate ratios may be used. Similarly, the ratio of elemental metal (e.g., by weight or volume) to matrix material (particulate or not) may be between about 1/100 and 100/1 (e.g., between 1/10 and 10/1, about 1/5 to 5/1, or about 1/2 to 2/1, or about 1/1).

In some aspects, elemental metal particles are incorporated (e.g., embedded) in a non-metallic plastic, rubber, silicone, polymeric, and/or adhesive matrix (e.g., an organic matrix). The resulting composition can be flexible and durable and provided in any suitable form, including, for example a sheet (e.g., a patch or strip) that is sufficiently flexible to readily conform to the shape of a body surface region to which it is applied.

In some aspects, an elemental metal composition may have a field effect on biological tissue (e.g., it may alter an electrostatic and/or electromagnetic field of a biological tissue). The field effect may be used to impact one or more biological processes. As used herein, a biological process may be impacted if it is altered in any manner. For example, a process may be enhanced (e.g., the amplitude, degree, and/or speed of the process may be increased). In other aspects, a process may be suppressed (e.g., the amplitude, degree, and/or speed of the process may be reduced). In further aspects, a process may be established, redirected, or terminated.

In one aspect, compositions of the invention may be used therapeutically to treat certain conditions in animals (e.g., humans, pets, agricultural animals, etc.). Conditions that can be treated include skin diseases, pain, inflammation, injuries, and other conditions described herein.

In another aspect, compositions of the invention may be used in agriculture and/or horticulture to alter certain aspects of plant physiology. In certain aspects, plant growth, seed germination, fruit and/or vegetable ripening, and/or other aspects of plant physiology may be modified as described herein (e.g., to preserve fruits or vegetables, to increase seed germination, etc.).

Elemental metal compositions of the invention may be prepared and/or packaged in different formulations and/or configurations depending on their intended use as described herein.

The present description provides details and examples of different elemental metals, coatings, and devices of the invention along with useful applications for animals and plants. It should be appreciated that different applications of the invention may involve different elemental metals, coatings, and/or containers. In addition, it should be appreciated that a predetermined electrostatic and/or electromagnetic field effect may not be the only factor that influences or determines the type of metal, coating, and/or container that is used for a particular application. For example, properties such as toxicity, availability, cost, ease of use, and other properties described herein, or any combination thereof may inform the choice of appropriate metal(s), coating(s), and/or container(s).

Aspects of the invention relate to compositions and devices comprising certain configurations of one or more elemental metals and methods for their use. Applicant has discovered that certain configurations of elemental metals may have therapeutic and/or biological effect(s) when contacted to a biological tissue surface. In one embodiment, and without wishing to be bound by theory, therapeutic and/or biological effect(s) are related to an electric field produced by an elemental metal composition, and not to specific chemical interactions between the elemental metal(s) and one or more biological molecules within a biological tissue.

As used herein, an elemental metal may be a transition metal, a metalloid, or other metal that can be stable as a free metal in nature. A transition metal may be scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, unnilnilium, unnununium, or unnunbium. Transition metals have valence electrons in more than one shell, and can exist in different oxidation states. Transition metals include metals that can produce a magnetic field (iron, cobalt, and nickel). A metalloid may be boron, silicon, germanium, arsenic, antimony, tellurium, or polonium. Some metalloids are semi-conductors (silicon and germanium). Other metals that can exist as free metals include aluminum, gallium, indium, tin, thallium, lead, and bismuth. These metals only have valence electrons in their outer shell and do not exist in more than one oxidation state.

In contrast, alkali metals and alkaline earth metals are not present as free metals in nature and are not elemental metals as used herein. Alkali metals include lithium, sodium, potassium, rubidium, cesium, and francium. Alkali metals are reactive metals with one electron in their outer shell and they readily lose this electron in an ionic bond with other elements. Alkaline earth metals include beryllium, magnesium, calcium, strontium, barium, and radium. Alkaline earth metals are also very reactive metals and are not stable as free metals in nature.

According to the invention, any elemental metal or combination of elemental metals may be included in a biologically effective composition if it imparts suitable electrical field properties to the composition (e.g., when coated with one or more non-metallic materials). However, it should be appreciated that certain biochemical properties may be considered and evaluated when choosing an elemental metal, even though the biological effectiveness of the composition does not depend on specific chemical interactions between the elemental metal and one or more biological molecules. For example, a composition preferably is not harmful (e.g., is non-toxic), particularly if it is not contained within a physical device that protects an animal, plant, or the environment from exposure to the composition. Accordingly, in some aspects one or more non-harmful metals are used. In another aspect, metals with different electrochemical properties may be combined to produce a composition with an appropriate capacitor and/or field effect when contacted with biological tissue. In yet another aspect, an elemental metal composition may include only (or primarily) elemental metal(s) that are naturally present in a biological tissue (animal or plant) that is being treated. For example, a composition for use with a human may include one or more of iron, copper, magnesium, and selenium. In one embodiment, the relative amounts of two or more elemental metals in a composition may be similar (e.g., the same or about the same) as their relative amounts in a biological tissue. However, in other aspects any one or more elemental metals may be included in a composition described herein. In one embodiment, any two or more different elemental metals (e.g., 2, 3, 4, 5, 6, 7, 8, 9, 10, 10-15, 15-20, or more) maybe combined. Two or more elemental metals may be included as a mixture or as an alloy. A composition may contain a combination of one or more elemental metal(s), and one or more alloys. Alternatively, a composition may contain only elemental metal(s) or only alloy(s). Ratios of different metals (e.g., in mixtures or in alloys) in different compositions of the invention may range from 1:1000 to 1000:1 (e.g., by weight). However, higher, lower, or intermediate ratios maybe used (e.g., 100:1, 50:1, 10:1, 5:1, 1:1, 1:5, 1:10, 1:50, 1:100, etc.). It should be appreciated that any combination of two or more (e.g., 3, 4, 5, 6, 7, 8, 9, 10, etc.) different elemental metals may be used. For example, a composition may include iron, zinc, copper, aluminum, silicon, or any combination of two or more thereof (e.g., all thereof). In some aspects, a composition may include iron and zinc. In some aspects, a composition may include iron and copper. In some aspects, a composition may include, zinc and copper. Any one of these compositions also may include aluminum, or silicon, or a combination or aluminum or silicon. In some aspects, the ratio of iron to zinc may be between about 10/1 and about 1/1 (e.g., 10/1, 5/1, 2/1, 1/1, for example by weight) or any higher, lower, or intermediate ratio. In some aspects, the ratio of zinc to copper may be between about 10/1 and about 1/1 (e.g., 10/1, 5/1, 2/1, 1/1, for example by weight) or any higher, lower, or intermediate ratio. In some aspects, the ratio of copper to aluminum may be between about 10/1 and about 1/1 (e.g., 10/1, 5/1, 2/1, 1/1, for example by weight) or any higher, lower, or intermediate ratio. In some aspects, the ratio of aluminum to silicon may be between about 10/1 and about 1/1 (e.g., 10/1, 5/1, 2/1, 1/1, for example by weight) or any higher, lower, or intermediate ratio. Any specific combination of the above ratios may be used in a composition of the invention. For example, a combination of particles of one or more (e.g., any 2 or 3, or all 4) of iron, zinc, copper, of aluminum can be present in any ratio of the four elements. For example a ratio of between about 20/1 and about 1/1 (e.g., about 15/1, about 10/1, or about 5/1, for example by weight) or iron relative to any of the other elemental metals can be used. In some aspects, a ratio of between about 10/1 and about 1/10 (e.g., about 5/1, about 1/1, about 1/5, for example by weight) between any two of zinc, copper, and/or aluminum can be used. In some aspects, a composition can also or alternatively include particles of one or more of the following metals: silver, gold, nickel, tin, carbon, cobalt, selenium, boron, and/or sulfur. In some aspects, a composition can also or alternatively include particles of steel, stainless steel, and/or bronze.

In a further example, iron, zinc, copper, aluminum, and silicon may be present in any ratio of the five elements relative to each other (for example, in relative order of iron/zinc/copper/aluminum/silicon from about 10,000/1,000/100/10/1 to about 1/1/1/1/1, e.g., about 16/8/4/2/1, about 20/4/2/2/1, about 8/4/2/2/1, about 50/10/2/1/1, about 50/50/25/25/1, about 50/25/5/5/1, for example by weight, or any other combination of ratios described herein).

In certain aspects, a composition may include oxidized or reduced forms of elemental metal(s). However, in some aspects, oxidized and/or reduced forms should not represent more than 50%, for example, not more than 25%, not more than 20%, not more than 15%, not more than 10%, not more than 5%, not more than 1%, not more than 0.1%, or not more than 0.01% of the weight or volume of the elemental metal in the composition.

In certain aspects, a composition may include metals that are non-elemental in addition to one or more elemental metals. However, in some aspects the non-elemental metal (s) do not constitute more than 50%, for example not more that 40%, 30%, 25%, 20%, 15%, 10%), 5%, 1%, or 0.1% of the weight or volume of metal in the composition. Accordingly, the elemental metal(s) may represent more than 50%, for example more than 60%, 70%, 75%, 80%, 85%, 90%, 95%, 99%, or 99.9% of the weight or volume of metal in the composition. However, the total elemental metal(s) may represent from more than 99% to less than 1% of the total weight or volume of a composition (e.g., about 90%, 75%, 50%, 25%, 20%, 15%, 10%, 5%, 1%, or more or less).

Accordingly, in some aspects, a composition or device includes only or at least 50%, 60%, 70%, 80%, 90%, 95%, 99%, or more non-ionic metal. In some aspects, an elemental metal is provided in an inert or non-reactive matrix or coating (e.g., carbonaceous) to prevent the production of ionic metals (e.g., borates, sulfates, etc.).

In one aspect, a composition of the invention includes one or more elemental metals in particulate form. Accordingly, in some aspects, an elemental metal is provided in an insoluble form within a matrix. The diameter of a metal particle may range from several mms (e.g., 1 cm) to several nms. However, in certain aspects bigger or smaller particles may be used. Accordingly, a metal particle may be about 1 mm in diameter, about 100 microns in diameter, about 10 microns in diameter, about 1 micron in diameter, about 100 nms in diameter, about 10 nms in diameter, about 1 nm in diameter. A composition may contain from one to dozens, hundreds, thousands, millions, billions or more particles per unit volume. The sizes of the particles in a preparation may be uniform (e.g., all having approximately the same diameter) or may be distributed across a range of diameters (e.g., a narrow range with for example 90% of the particles within a two to tenfold range of diameter size, or a broader range with for example 90% of the particles within a 100 to 1,000 fold range of diameter size). Accordingly, compositions of the invention may include metal balls, metal filings, metal powders, nano-particles (e.g., particles between 0.1 to 10 nm in diameter). In one embodiment, particles have a diameter that is less than about 100 microns, for example less than about 50 microns, or less than about 10 microns. For example, particles with a diameter of about 40 microns or less may be selected using a 325 mesh sieve which excludes particles with a diameter greater than about 40 microns. It should be appreciated that the shape of the metal particles is not necessarily spherical. A metal particle may be a sphere or approximated to a sphere in some aspects. However, in other aspects, a particle may be ovoid, elongated, rectangular, irregular, etc. It should be understood that the reference to a diameter in the context of a particle relates to an average dimension across the particle. In the context of a sphere, a diameter is the diameter of the sphere. In the context of a less-spherical, or non-spherical particle, a diameter refers to an average dimension of the particle (e.g., an average of the longest distance, an average of the shortest distance, or an average of all distances, between two sides of the particle).

Particles of different sizes may be obtained or prepared using any suitable method. In one embodiment, particle sizes may be selected by sieving elemental metal particles using different meshes (e.g., 200 mesh, 300 mesh, 325 mesh, etc.).

These and other aspects of different elemental metals that can be used are described in more detail herein.

In one aspect, compositions and/or devices contain at least one elemental metal coated with a layer or within a matrix of non-metallic material (e.g., a layer or matrix of one or more non-conducting or semi-conducting materials). In another aspect, compositions and/or devices contain at least one elemental metal mixed with a preparation of non-metallic material (e.g., particles of one or more non-conducting or semi-conducting materials). According to the invention, a matrix (e.g., a coating) that separates at least a fraction (e.g., 100% or less, for example, about 80%, 70%, 60%, 50%, 40%, 30%, 20%, 10%, 5%, or less) of the elemental metal particles from each other may enhance one or more electrical properties of the composition.

Coatings may be organic material(s) (e.g., organic waxes, etc.), synthetic material(s), or any combination thereof. Examples of suitable coating materials include VASELINE® (Conopco, Inc. d/b/a Unilever), petroleum jellies, oils, beeswax, lanolin, etc.). It should be appreciated that certain materials may be used i) as coating materials to impart suitable electrical properties (e.g., conductance, field-effect, capacitance, etc.) on an elemental composition and/or ii) as mixture components to impart suitable physical properties (e.g., viscosity, malleability, etc.) on an elemental composition. For example, lanolin may be used as a coating and/or as an emulsifier. In some aspects, a material (e.g., lanolin) may be used primarily for its physical effect on a composition (e.g., an emulsifier). In some aspects, an oil (e.g., a mineral, animal, and/or a vegetable oil) may be used to modify one or more physical properties (e.g., to increase stickiness). In some aspects, an animal fat may be used as the matrix or may be added to a different matrix to modify one or more physical properties. In some aspects, one or more other materials or compounds may be used to increase or decrease the malleability, flexibility, and/or stickiness of a composition. However, their effect on the electrical properties of the composition also should be considered (e.g., evaluated experimentally).

In some aspects, elemental metal particles are incorporated (e.g., embedded) within a flexible matrix of plastic, rubber, resin, and/or colloidal material.

In one aspect, a preparation of elemental metal particles may be mixed with particles of a non-conducting or semi-conducting material (e.g., glass, silicone, wool, cotton, etc.). Any suitable ratio may be used. In one embodiment, the size range of the particles of elemental metal may be the same as that of the non-conducting or semi-conducting material. In one embodiment, the size range of the particles of elemental metal may be different from that of the non-conducting or semi-conducting material.

In one aspect, a composition may be viscous or semi-solid (e.g., waxy) at room temperature (or other temperature that is characteristic of the environment of use) so that it is easy to apply to a surface (e.g., skin). However, in certain aspects, a composition may be liquid at room temperature (or other temperature that is characteristic of the environment of use).

In yet other aspects, a composition may be solid or grainy at room temperature (or other temperature that is characteristic of the environment of use). Liquid solutions may be particularly useful to surfaces where physical spreading of a cream/ointment is not practical (e.g., for spreading/spraying over relatively large areas (e.g., agricultural areas). However, solid compositions also may be used in situations where a large number of units or volumes of an elemental metal composition may be dispersed over a large area (e.g., an agricultural area). Any form of composition may be contained within an enclosure (e.g., a container such as a solid container, a pouch, a sac, etc.). In aspects, a composition of the invention may be provided as an aerosol or other form that can be readily dispersed over an area of interest (e.g., a spray that can be sprayed onto a patient skin or a spray that can be sprayed over plants in a greenhouse or on a field).

In some aspects, a composition is rubbery or flexible and can be produced in the form of a sheet or patch that can be applied to the skin surface of a subject.

Figure 2:
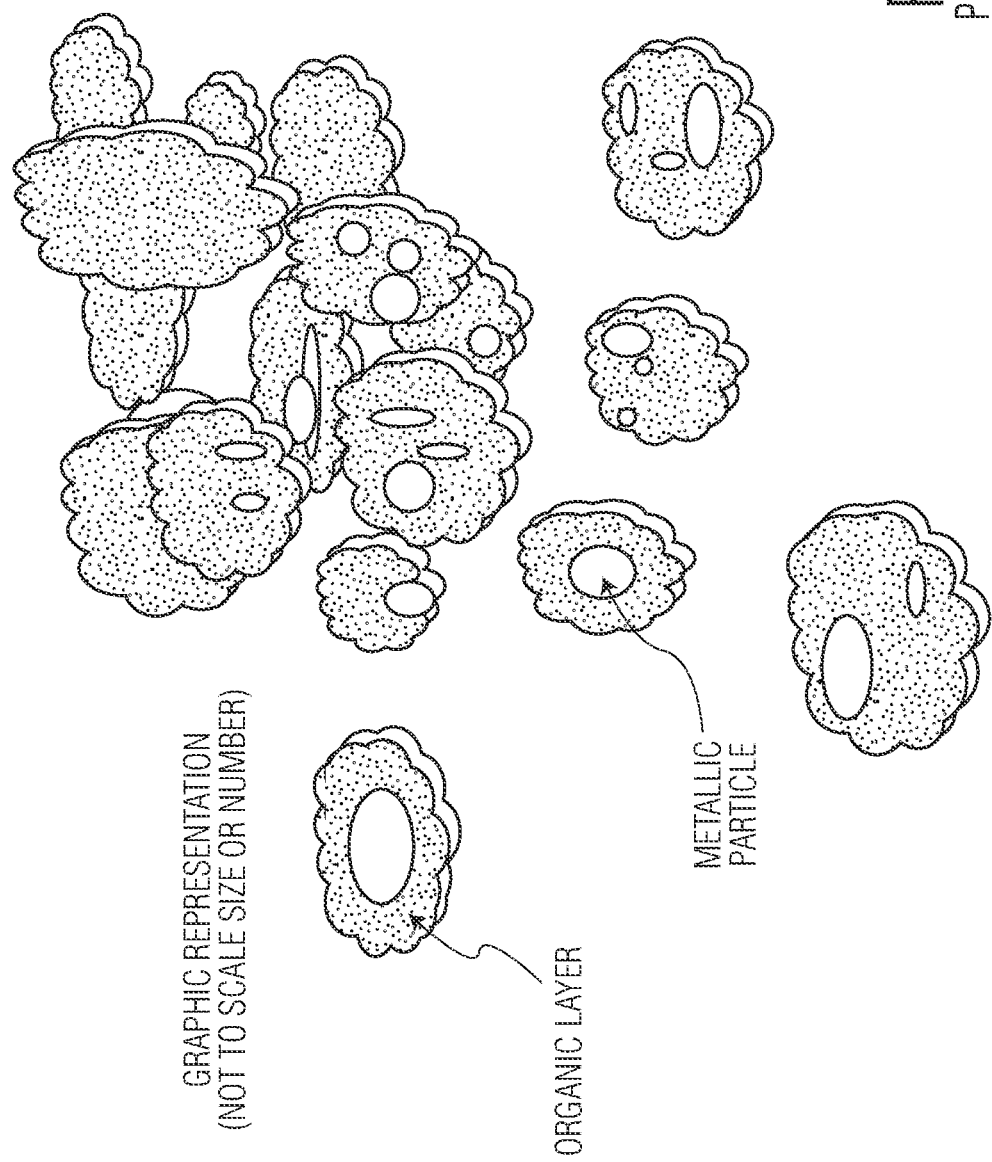
FIG. 2 illustrates a composition including elemental metal particles within a matrix of non-conducting or semi-conducting material (the composition as shown includes air pockets, however, in other aspects a composition may have few or no air pockets)

In one aspect, a coating is sufficiently malleable to be mixed with an elemental metal so that the coating covers at least a portion of the elemental metal surface thereby forming an interface between the elemental metal(s) and the coating material(s). In one embodiment, the coating may cover between 1% and 100%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% of the surface of the elemental metal (e.g., when inspected visually). FIG. 2 illustrates an example of several metal particles that are covered with a coating material.

In one embodiment, an elemental metal may be covered with a coating material under conditions that are suitable for preparing a mixture with the coating material covering the elemental material or a portion thereof (e.g., a wax may be mixed with elemental metal at a temperature sufficiently high to melt the wax). The resulting preparation subsequently may be used under different conditions (e.g., at a lower temperature).

As with the elemental metals, different properties may be considered when selecting an appropriate coating material. Properties may include conductivity, toxicity, availability, malleability, stability, etc., or any combination of two or more thereof.

It should be appreciated that similar elements and considerations may be used when preparing a composition with a particulate matrix (or a matrix that contains both particulate material and non-particulate coating material). In addition, the average size of matrix particles may be similar or different from the average size of the elemental metal particles in a composition.

In some aspects, different ratios of elemental metal particles to matrix particles and/or matrix material (e.g., if the matrix is a gel, rubber, colloidal material, plastic, or other polymer) may be used (e.g., about 1000:1; 100:1; 10:1; 1:1; 1:10; 1:100; 1:1000; or higher, lower, or intermediate ratios, for example by weight).

Accordingly, in different aspects of the invention, matrix materials may be solid, liquid, particulate, non-particulate, or a combination of two or more thereof.

In some aspects, different materials (e.g., elemental metals and/or matrix materials) may be selected based on their electrical properties, while also considering certain properties such as toxicity, availability, cost, etc. As described herein, different properties of materials including elemental metals and provide groupings of elemental metals and other materials based on properties that may be useful for certain applications. It should be understood that different properties described herein for individual metals may be considered for compositions including only one elemental metal, a mixture of two or more elemental metals, an alloy of two or more metals, or any combination of two or more thereof. However, certain metals may be less toxic when in combination with other elements. For example, certain metals may be less toxic or hazardous when in an alloy than when present as a pure metal. It also should be appreciated that elemental metals and matrix materials are evaluated and selected to have suitable electrical properties as described herein in addition to considering other factors.

In one aspect, safety and health considerations may be considered when selecting or using a material or element. In one embodiment, compositions may include only non-hazardous and/or non-radioactive metals (i.e., no hazardous and/or radioactive metals). In one embodiment, compositions may include only non-hazardous and/or non-radioactive alloys (e.g., alloys that contain no metals that are inherently hazardous and/or radioactive).

The hazardous properties of a metal may be rated according to HMIS (Hazardous Materials Information System). In one embodiment, non-hazardous metals are those with a health rating of 2 or lower (ratings typically range from 0-4).

In one embodiment, a composition of the invention does not contain any of the following radioactive elements: technetium, bismuth, (metalloids) polonium and astatine, actinium, thorium, protactinium, uranium, neptunium, plutonium, americium, curium, berkelium, californium, einsteinium, fermium, mendelevium, nobelium, lawrencium, rutherfordium, dubnium, seaborgnium, bohrium, hassium, meitnerium, darmstadtium, unununium, ununbium, ununtrium, ununquadium, ununpentium, ununhexium and radioactive elements that are higher on the periodic table. However, one or more such elements may be used in certain aspects, for example by providing them in a shielding container or device that reduces the amount of damage that may be caused by radiation. Also, certain radioactive metals emit a low energy radiation and may be used without a shielding container or device. For example, indium is only slightly radioactive (beta decay), is not harmful, and may be useful in compositions and methods of the invention. Similarly, other slightly radioactive metals may be used.

In one embodiment, a composition of the invention does not contain a spontaneous combustible or explosive solid element or an element with any other dangerous physical property. For example, individual metals with Hazardous Material Information System (HMIS) ratings of 3 or greater in flammability and other health properties may be excluded from compositions of the invention (except in the form of an alloy or mixture that is not as physically dangerous). Examples of metals and alloys that may be physically dangerous include, Lanthanum, Manganese, Hafnium (10 micron particles spontaneously ignite), Osmium, and Phosphorus.

Similarly, in certain aspects metals that are generally (grossly) toxic may be excluded from compositions of the invention. Examples of metals that may be toxic to animal or plant life include (especially at high concentrations) Hafnium, Tungsten, Manganese, Chromium, Osmium, Cobalt, Thallium, Phosphorus, Mercury, Arsenic, and Lead. However, in one embodiment, any of these metals may be non-toxic or less toxic when used as a stable alloy (e.g., a manganese, chromium, or phosphorous alloy). Also, certain of these metals (e.g., manganese and cobalt) may be important metals for the growth of some organisms (e.g., plants) and therefore non-toxic when used in suitable amounts (e.g., relatively low concentrations).

Other toxic metals include those with multiple toxicities as determined by Occupational Safety and Health Administration (OSHA) and Department of Environmental Protection (DEP), for example Cadmium, Hafnium, Antimony, Mercury, Arsenic, Lead, Osmium, and Cobalt. In other aspects, metals that are toxic when inhaled may be excluded (e.g., Hafnium, Tungsten, Manganese, Osmium, Cobalt, Cadmium, Thallium, Phosphorus, Antimony, Arsenic, and Lead). In other aspects, metals that are toxic when ingested orally may be excluded (e.g., Cobalt, Cadmium, Thallium, Phosphorus, Antimony, Arsenic, and Lead). In further aspects, metals that are toxic when absorbed through the skin, and/or metals that are skin irritants, and/or metals that cause ulcerations may be excluded. Examples of such metals include Hafnium, Manganese, Osmium, Cobalt, Thallium, Phosphorus, and Arsenic. In yet further aspects, CNS toxic elements or alloys that contain these elements may be excluded (e.g., Tungsten, Manganese (Parkinson's), Lead, Antimony, and Mercury). In other aspects, toxic metals and/or alloys that destroy mucosal membranes and/or skin may be excluded (e.g., Chromium, Osmium, Thallium, and Phosphorus). In certain aspects, metals that are toxic to plants may be excluded (e.g., Aluminum at high concentrations). In other aspects, carcinogen metals (e.g., as defined by Occupational Safety and Health Administration, Food and Drug Administration, or other organizations) may be excluded (e.g., Zirconium, Chromium, Tungsten, Cobalt, Nickel, Cadmium, Thallium, and Alloy of Chromium-Nickel-Cobalt). However, it should be appreciated that any one of more of these elements may be used if provided in a suitable container or protective device that reduces any undesirable properties of the metals to an acceptable level in view of the anticipated exposure to animal (e.g., human) and/or plant.

According to aspects of the invention, nuisance metals may be excluded. However, in many aspects nuisance metals may be used if the nuisance factor does not outweigh the anticipated or observed physiological benefit. Nuisance metals may have an HMIS rating of 2 on health exposure. Non-limiting examples of nuisance metals include: Scandium (Flammability 2—powder, Health 1—inhalation, Reactivity 0); Yttrium (Flammability 3—powder spontaneous ignition, Health—1, Reactivity 0); Titanium (Flammability 3—powder, Health 1—inhalation, Reactivity 1); Vanadium (Flammability 0, Health 2—chronic inhalation, Reactivity 0) is used in medical devices; Niobium (Flammability 0, Health 0, Reactivity 0); Tantalum (Flammability 0, Health 1—inhalation, Reactivity 0); Molybdenum (Flammability 0, Health 0, Reactivity 0); Rhenium (Flammability 0, Health 0, Reactivity 0); Iron (Flammability 0, Health—ingestion 2, Reactivity 0); Ruthenium (Flammability 1, Health 1, Reactivity 0); Rhodium (Flammability 1, Health 1, Reactivity 0); Iridium (Flammability 1, Health 0, Reactivity 0); Nickel (low overall toxicity except on ingestion and then carcinogenic and reactivity is low); Palladium (Flammability 0, Health 1—inhalation, Reactivity 0); Platinum (Flammability 0, Health 1, Reactivity 0); Copper (Flammability 2—dust, Health 1, Reactivity 1) ; Silver (Flammability 2—powder, Health 1—skin absorption—Argyrosis, Reactivity 1); Gold (Flammability 1—powder, Health 1—ingestion, Reactivity 0); Zinc (Flammability 1—powder, Health 1—fume ingestion, Reactivity 0); Aluminum (Flammability 1—powder, Health-ingestion, Reactivity 2—exothermic with iron and water); Gallium (Flammability 0, Health 1—ingestion, Reactivity 0); Indium (Flammability 0, Health 1—ingestion, Reactivity 0); and Tin (Flammability 3—powder, Health 2—inhalaton, Reactivity 0).

Non-limiting examples of nuisance metalloids include: Boron (Flammability 3—powder spontaneous ignition, Health 2—toxic fumes if burning & ingestion, Reactivity 0); Silicon (Flammability 0, Health 1—inhalation, Reactivity 0); Germanium (Flammability 0, Health 0, Reactivity 0); and Tellurium (Flammability 0, Health 3—ingestioin, inhalant, Reactivity 0). It should be appreciated that nuisance metalloids may be used in certain aspects if appropriate protective measures are taken.

Non-limiting examples of nuisance non-metals that may be used as a matrix (e.g., a coating) include Carbon (Flammability 1—powder Health 0, Reactivity 0); Sulfur (Flammability 1—powder, Health 1—ingestion, Reactivity 0); and Selenium (Flammability 1—powder, Health 1—inhalation, Reactivity 1).

In some aspects of the invention, compositions may exclude materials (e.g., metals) that cause acute inflammation or that are readily absorbed through the skin of an animal (e.g., a human). However, such metals may be used if they are used in low amounts or if they are provided in a container or suitable device that protects the skin from direct contact with the metal. Non-limiting examples of such metals include: Ruthenium (strongly stains skin); Nickel and Silver (Argyrosis).

According to aspects of the invention, useful elements (e.g., elemental metals and alloys) that are readily available in particulate form and at a reasonable cost include: Yttrium, Titanium, Vanadium, Molybdenum, Iron, Nickel, Palladium, Copper, Silver, Zinc, Boron, Aluminum, Gallium, Indium (shot), Carbon, Silicon, Germanium, Tin, Sulfur, Selenium, and Tellurium. Other useful metals that may be more expensive include: Scandium, Niobium, Tantalum, Rhenium, Ruthenium, Rhodium, Iridium, Platinum, and Gold.

According to aspects of the invention, the following useful elements and alloys may cause some/minor skin irritation (HMIS 0 or 1) in finely divided form: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Boron, Aluminum, Gallium, Indium, Silicon, Germanium, Tin, Sulfur, Selenium, and Tellurium.

Elements that may be readily available in particulate or finely divided powder or nanoparticle forms include: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Boron, Aluminum, Indium, Carbon, Silicon, Germanium, Tin, Sulfur, Selenium, and Tellurium (note that Gallium may be available as soft/liquid).

According to aspects of the invention, the following elements should be used with care to prevent ingestion by an animal (e.g., a human) or leaching into the environment: Yttrium, Scandium, Titanium, Vanadium, Tantalum, Molybdenum, Rhenium, Iron, Ruthenium, Rhodium, Iridium, Nickel, Palladium, Platinum, Copper, Silver, Gold, Zinc, Boron, Aluminum, Gallium, Indium, Carbon, Silicon, Germanium, Tin, Sulfur, Selenium, and Tellurium. Certain of these elements may be non-toxic or even beneficial in low amounts but toxic in higher amounts (e.g., vanadium which is an essential element required in low amounts for some biological tissue or organisms including lower invertebrates, but often toxic in higher amounts). Niobium also should be used with care as it may cross the placental barrier in animals.

In other aspects of the invention, the following elements may be particularly useful for agricultural applications: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Boron, Aluminum, Gallium, Indium, Carbon, Silicon, Germanium, Tin, Sulfur, Selenium, and Tellurium. For example, sodium, potassium, calcium, magnesium, phosphorus, and sulfur may be essential macronutrients for certain plants. Chlorine, iron, boron, manganese, zinc, copper, molybdenum, and nickel may be essential micronutrients for certain plants. In addition, silicon, sodium, cobalt, and selenium may be beneficial elements for certain plants.

Although less expensive and readily available elements (e.g., metals) may be selected, it should be appreciated that any of the metals described herein may be used in aspects of the invention. Examples of elements that may be readily obtained and that are relatively inexpensive in finely divided form include: Titanium, Vanadium, Molybdenum, Iron, Nickel, Palladium, Copper, Silver, Zinc, Boron, Aluminum, Indium, Carbon, Silicon, Germanium, Tin, Sulfur, Selenium, and Tellurium. Examples of other elements that may be used but that are more difficult to obtain and/or more expensive include: Yttrium, Scandium, Niobium, Tantalum, Rhenium, Ruthenium, Rhodium, Iridium, Platinum, Gold, and Gallium (soft).

In some aspects of the invention, elements and alloys that have FDA approval may be selected for certain human applications. Examples include: Titanium (approved for implants and coatings); Vanadium (approved for implants and coatings); Tantalum (approved for implants, dental and surgical instruments); Molybdenum (approved for prosthetic devices, trace element in plants and animals); Iron (essential element, approved for supplements, and has multiple approvals); Iridium (approved for surgical tools); Palladium (approved for multiple uses in alloys); Platinum (approved for multiple uses); Copper (approved for multiple uses); Silver (approved for multiple uses); Gold (approved for multiple uses); Zinc (approved for multiple uses); Carbon (approved for multiple applications); Silicon (approved for multiple uses); Germanium (alloy, approved for uses); Tin (approved for multiple uses); Sulfur (approved for multiple uses); and Selenium (approved for multiple uses). It should be appreciated that compositions of the invention may be used for these and/or other uses. However, the fact that a compound has been approved for one use suggests that it may be suitable (e.g., non-toxic, non-irritant, etc.) for other uses.

It should be appreciated that certain metals that are individually toxic may have reduced toxicity when in the form of an alloy or mixture. Relative toxicities may be determined by one of skill in the art and appropriate alloys may be selected based on their toxicity profiles.

In one aspect, one or more alloys listed with American Iron and Steel Institute (AISA) may be used, for example, Iron Alloys with: Aluminum, Silicon, Manganese, Chromium, Vanadium, Molybdenum, Niobium (columbium), Selenium, Titanium, Phosphorus, Cobalt, Tungsten, Boron, Iron-Carbon Alloys with: Silicon, Phosphorus, Sulfur, Manganese, Nickel, Chromium, Molybdenum, Copper, and/or Titanium.

In one aspect, prosthetic alloys may be used. For example, strongly adherent and passivating surface oxides, such as titanium oxide (Ti02) on titanium-based alloys and chromium oxide (Cr203) on cobalt-based alloys may be used.

In one aspect, ferrous, cobalt-based, or titanium-based alloys may be used: for example, cold-worked stainless steel; cast Vitallium; a wrought alloy of cobalt, nickel, chromium, molybdenum, and titanium; titanium alloyed with Aluminum and vanadium; and commercial-purity titanium may be used.

In one aspect, certain alloys may be modified by nitriding or ion-implantation of surface layers of enhanced surface properties. For example, one or more of the following alloys may be used: as cast Co—Cr—Mo alloy; Bronze: copper and tin plus traces of other elements; Brass: copper and zinc; Bearing alloys: Babbitt metal, tin (Sn), antimony (Sb) and copper (Cu), copper, or silver (Ag); Corrosion-resisting alloys: Stainless steels: Austenitic, Ferritic and Martensitic formulas; Aluminum alloys: Al-lithium, chromium (Cr), nickel (Ni), Monel, an alloy of nickel and copper; Inconel: which contains chromium and iron (Fe), Spiegeleisen: iron-manganese-carbon-silicon; Dental alloys: Amalgams silver and mercury (Hg), tin, copper, and zinc (Zn), Gold-base (Au), silver, and copper, palladium and platinum; Vitallium an alloy of cobalt, chromium, molybdenum, and nickel; Die-casting alloys: Zinc-base: aluminum and copper; Aluminum-base: Silicon, copper, iron, silicon; Eutectic alloys: copper with silver, tantalum carbide (TaC) fibers in a matrix of a cobalt-rich alloy; Fusible alloys: lead, cadmium, bismuth, tin, antimony, and indium, bismuth; and/or, Inter metallics: Mu-metal (nickel-iron-copper-molybdenum).

In one aspect, high-temperature alloys may be used, including one or more of: Stainless steels: Cr, Ni, and molybdenum; both nickel-base and cobalt-base alloys, Nichrome, a nickel-base alloy containing, chromium and iron; Rene-41 contains, chromium, aluminum, titanium (Ti), cobalt (Co), molybdenum, iron, carbon (C), boron (B), and nickel; and/or Molybdenum-base alloys.

In one aspect, joining alloys may be used. For example, one or more of the following may be used: copper-zinc, tin brass, silicon-aluminum eutectic alloy, aluminum-containing magnesium, and/or lead-tin alloys.

In one aspect, light-metal alloys may be used. For example, one or more of the following may be used: Aluminum and magnesium (Mg), aluminum and copper, and magnesium and aluminum; ternary (three-element) and/or more complex: aluminum-zinc-magnesium systems.

In other aspects, any one or more of the following alloys may be used: low-expansion alloys (e.g., Invar (iron-nickel), Kovar (5 iron-nickel-cobalt), etc.); magnetic alloys (e.g., silicon-ferrite); permalloy (nickel-iron) and some comparable cobalt-base alloys; ceramic ferrites; lnicos, Alnico-4 (iron-nickel-aluminum-cobalt), RCo5, where R is samarium (Sm), lanthanum (La), cerium (Ce); precious-metal alloys (e.g., yellow gold which is an Au—Ag—Cu alloy, white gold which is Au-nickel, silver, or zinc, which change the color from yellow to white); the alloy platinum (Pt)-rhodium (Rh)-platinum; sterling silver; shape memory alloys; gold alloyed with cadmium; nickel and titanium known as nitinal; thermocouple alloys; Chromel: nickel and chromium; Alumel: nickel, aluminum, chromium, and silicon; the widely used Chromel-Alumel thermocouple; superconducting alloys (e.g., niobium and titanium, niobium and tin, vanadium and gallium, niobium and germanium, niobium and aluminum, etc.); lead-indium; lead-gold (PbAu); ceramic; copper oxide-based materials; yttrium-barium-copper-oxygen; bismuth-strontium-calcium-copper-oxygen; thallium-barium-calcium-copper-oxygen; etc.; or any combination of two or more of the above.

It should be appreciated that the electrical properties of a composition described herein depend in part on the types of elemental metal and non-metallic matrix materials that are used. In some aspects, an elemental metal-containing composition described herein may be evaluated or selected based on measured electrical properties (e.g., to have an output and/or optimal response within a frequency range of about 0.01 Hz to about 100 Hz, for example from about 0.1 Hz to about 10 Hz, for example, between 0.2 Hz and 5 Hz, between 0.5 Hz and 4 Hz, for example around 1 Hz, around 2 Hz, or around 3 Hz; and/or to have a voltage output or optimal response within a voltage range of about 0.1 mV to several Vs as described herein, for example around 10 mV, around 50 mV, around 100 mV, around 250 mV, or around 500 mV).

Also, the following non-limiting properties may be considered when determining which metals or mixtures of metals to use: electroresistivity, electron-nucleus "charging characteristics," reduction or oxidation potential, electrostatic properties, electro-negative characteristics, electro-positive characteristics. In addition, one or more compositions having suitable electrical properties can be tested and/or optimized for their effect on different biological systems. Accordingly, one of ordinary skill can optimize a composition of the invention for a particular use.

In one aspect, elements that due to their particular electroresistivity (micro ohm-cm @ normal conditions) may be useful in elemental metal compositions of the invention include elements with high or low electroresistivity. Different electroresistivity properties may be used depending on the biological application and the desired biological effect (e.g., the desired intensity of the biological effect). Suitable electroresistivity also may be influenced by other metals in the composition and by the coating material(s) and the configuration of the final compositions (e.g., an ointment or cream, or enclosed within a container, etc.). Accordingly, in some aspects an elemental metal composition may include one or more of a low resistivity, semi-conductor, or high resistivity (electron deficient and/or nonmetal) metal(s).

In one aspect, low resistivity metals include: Yttrium, Scandium, Titanium, Vanadium, Niobium, Tantalum, Molybdenum, Rhenium, Iron, Ruthenium, Rhodium, Iridium, Nickel, Palladium, Platinum, Copper, Silver, Gold, Zinc, Aluminum, Gallium, Indium, Silicon, and/or tin.

In one aspect, semi-conductors (Metalloids) include: Boron, Silicon, Germanium, and/or Tellurium.

In one aspect, high resistivity elements include: Boron (electron deficient), Carbon, Germanium, Silicon, Sulfur, Selenium, and/or Tellurium.

In one aspect, elements that due to their electron-nucleus "charging characteristics" in the form of electronegativity (Pauling) may be useful in elemental metal compositions of the invention include those that are not so high as to be dangerously reactive. However, it should be appreciated that combinations of high and low electronegativity may yield compositions with a high "capacitance." Different electronegativity properties may be used depending on the biological application and the desired biological effect (e.g., the desired intensity of the biological effect). Suitable electronegativity also may be influenced by other metals in the composition and by the coating material(s) and the configuration of the final compositions (e.g., an ointment or cream, or enclosed within a container, etc.).

In one embodiment, compositions contain one or more metals with electronegativity values between 1.2 and 2.56 Paulings. For example, Molybdenum (1.16), Scandium (1.3), Yttrium (1.3), Aluminum (1.5), Titanium (1.5), Tantalum (1.5), Vanadium (1.6), Niobium (1.6), Zinc (1.6), Gallium (1.6), Indium (1.7), Silicon (1.8), Iron (1.8), Nickel (1.8), Tin (1.8), Copper (1.9), Silver (1.9), Rhenium (1.9), Germanium (2.01), Boron (2.04), Tellurium (2.1), Rhodium (2.2), Platinum (2.2), Palladium (2.2), Ruthenium (2.2), Iridium (2.2), Gold (2.4) Sulfur (2.5), Carbon (2.55), and/or Selenium (2.55).

In one aspect, elements that due to their relatively low, medium or high oxidation potential may be particularly useful in elemental metal compositions of the invention may nonetheless have special handling considerations as discussed herein.

In one aspect, low oxidation potential metals include: Gallium, Indium, Silicon, Nickel, Tin, Copper, Silver, Ruthenium, Germanium, Boron, Tellurium Rhodium, Iridium (mildly basic), Palladium, Platinum, Gold, Carbon, and/or Selenium.

In one aspect, moderate oxidation potential metals (e.g., metals with some instability when exposed to flame, air, oxygen, or water) include: Aluminum, Zinc, Iron, Titanium, Niobium (5 micron spontaneous ignition in air), Tantalum, and/or Rhenium.

In one aspect, elements with combined extremes in reduction-oxidation potential (in solution versus hydrogen electrode) may be particularly useful in certain combinations.

In one aspect, elements with high electro-positive potential (reactive chemically) include: Yttrium, Scandium, Titanium, Vanadium, Ruthenium, Nickel, Niobium, Zinc, Iron, Aluminum, Gallium, Indium, Tin, Sulfur, Selenium, and/or Tellurium. In one embodiment, elements with high electro-negative potential (least reactive chemically) include: Copper, Silver, Gold, Rhodium, Platinum, and/or Palladium.

In one aspect, elements with a moderate degree of negative reduction potential (between about 1.8 and 2.0 Paulings) may be useful in some elemental metal compositions of the invention for human use. For example, Zinc, Gallium, Indium, Silicon, Iron, Nickel, Tin, Copper, and/or Silver may be used. In one embodiment, these elements form particularly effective energy compounds when mixed with elements from the extremes of the electromotive series. For example, one or more elements with a moderate degree of negative reduction potential may be mixed with one or more elements below 1.6 Pauling such as Molybdenum (1.16), Scandium (1.3), Yttrium (1.3), Aluminum (1.5), Titanium (1.5), Tantalum (1.5), Vanadium (1.6), and/or Niobium (1.6). In another example, one or more elements with a moderate degree of negative reduction potential may be mixed with one or more elements above 1.9 Pauling such as Rhenium (1.9), Germanium (2.01), Boron (2.04), Tellurium (2.1), Rhodium (2.2), Platinum (2.2), Palladium (2.2), Ruthenium (2.2), Iridium (2.2), Gold (2.4) Sulfur (2.5), Carbon (2.55), and/or Selenium (2.55).

In one aspect, elements with particular electrostatic properties may be useful in elemental metal compositions of the invention. For example, tantalum may be useful, because it has the most capacitance per volume of any substance. Ruthenium may be useful, because it has multi-valence states and high capacitance. Boron may be useful in some aspects, because it has poor thermal and electrical conductivity. Gallium may be useful in some aspects, because it is a "poor metal" and soft/liquid. Indium may be useful in some aspects, because it has a unique response to electric fields. Carbon may be useful in some aspects as a coating or other matrix. Carbon also may be used in one or more alloys (e.g., carbon steels), because it has multiple forms with variable electrostatic properties. Silicon may be useful in some aspects, because it is a stable semiconductor. Germanium may be useful in some aspects, because it is a semi-conductor and has a unique response to infra-red radiation. Sulfur may be useful in some aspects, because it has multiple crystalline morphologies. Selenium may be useful in some aspects, because of its rectifier functions and it is radiant to electrical energy. Tellurium may be useful in some aspects, because it is slightly photosensitive.

In one aspect, "poor metals" or "post transition metals" may be used (metals occurring between metalloids and transition metals that are more electropositive than many transition metals). For example, Aluminum, Gallium, Indium, and/or Tin may be used.

In one aspect, certain elements and/or alloys may be particularly useful in elemental metal compositions of the invention. For example, metals with a non-chemical bonding and/or an inducible and/or fluctuating electrostatic "field effect" may be particularly useful. In one embodiment, Yttrium, Scandium, Molybdenum, Palladium, Silver, Zinc, Aluminum ("elemental clustering"), Iron, Copper, Gallium, Indium, Carbon, Silicon, Germanium, Sulfur, Selenium, and/or Tellurium may be particularly useful.

In one aspect, elements and alloys that have ferromagnetic potential (ferro-magnetic group) may be non-toxic and useful for compositions of the invention. For example, Iron, Cobalt Nickel, Platinum, and/or Yttrium (slight magnetic susceptibility) may be used.

In one aspect, metals in the Platinum metal group may be useful, for example, Platinum, Palladium, Ruthenium, Rhodium, and/or Iridium. In one embodiment, Osmium is not used.

Any suitable methods for producing devices or compositions described herein can be used. In some aspects, metal particles can be mixed with a polymer, gel, colloidal material or other matrix material before the matrix material solidifies (e.g., by polymerizing, setting, curing, or otherwise solidifying), for example, to form an elastic and/or flexible composition that can be placed on a subject.

According to the invention, certain metal powders may be thermally unstable in the presence of oxygen, because the powders possess a high surface area per unit mass. Very fine metal powders can burn in air (pyrophoricity) and are potentially explosive. Therefore clean handling of powder may be important. Suitable methods for handling powders may include venting, controlled oxidation to passivate particle surfaces, surface coating, minimization of sparks or heat sources, etc., or any combination thereof. Some respirable fine powders pose a health concern and can cause disease or lung dysfunction: the smaller the particle size, the greater the potential health hazard. Control is exercised by the use of protective equipment and safe handling systems such as glove boxes, respirators, masks, air-handling devices, filters, etc.

In one embodiment, compositions of the invention may be prepared under conditions that prevent or minimize oxidation and/or reduction of the elemental metals (e.g., prevent or minimize exposure to humidity and/or oxygen (e.g., time and/or amount)).

Elements and alloys (that may contain these elements) that are useful to the formulation of elemental metal compositions of the invention may require special handling with precautions in finely divided forms determined by OSHA regulations. All may have respiratory exposure limits (due to irritation, but not biological toxins except at high doses of particulates or fumes) defined by OSHA for finely divided form. Certain elements may require special care due to skin irritation, known allergens, and may be absorbed (or cross) through inflamed skin, relatively low (HMIS ratings on flammability-will ignite as powder with a heat source, and health effects, environmental and chemical reactivity generally low HMIS #1 or less).

Compositions of the invention may be mixed using any suitable method to obtain elemental metal(s) coated with sufficient coating material(s) in order to exhibit desirable field effect properties.

In some aspects, additional materials may be added to an elemental metal composition to improve certain physical characteristics (e.g., malleability). For example an emulsifier such as lanolin may be added. Alternatively, other types of materials may be added, e.g., for stability, to prevent moisture, to prevent oxidation, to prevent microbial growth, etc. (e.g., sulfur, antioxidant(s), vitamin(s), other stabilizers).

In one embodiment, compositions may be prepared so that they are suitably malleable to be molded to fit a particular shape such as the individual shape of a subject's anatomical region that is to be treated (e.g., joint, back, etc.) or a plant feature. The composition may be molded during preparation to fit a form. Alternatively, the composition may be molded when applied to a subject or plant.

In some aspects, compositions can be prepared by including an activation step that increases the responsiveness of biological tissue when exposed to the activated composition. Examples of activation include heat (e.g., during or after mixing, or both), exposure to a source of electro-magnetic radiation (e.g., a Tesla coil); exposure to sunlight; exposure to the air; exposure to a source of ionizing radiation; exposure to electric current (e.g., by inserting electrodes into the composition and applying an alternating or direct current to the electrodes); exposure to a negative ion generator; etc.; or any combination of two or more of the above.

The ratio of elemental metal to coating material may range from 1:1,000 to 1,000:1 by weight or volume. However, higher, lower, or intermediate ratios may be used. For example, ratios of 100:1, 50:1, 10:1, 5:1, 1:1, 1:5, 1:10, 1:50, or 1:100 may be used. The appropriate ratio may depend on the nature of the metal (e.g., the size of the particles), the nature of the coating material (e.g., how waxy or oily it is), and the intended use (e.g., whether the composition is intended as a cream to be applied to skin or whether it will be provided in a container or a sealed device).

Elemental compositions of the inventions may be formulated as creams, ointments, etc. In one embodiment, a cream or ointment may be manufactured based on a coated elemental metal preparation. In another embodiment, elemental metal(s) (e.g., particulate elemental metal(s)) may be added to an existing cream or ointment. The elemental metal(s) may be added in a coated form. Alternatively, the elemental metal(s) may be added without a coating and the components of the cream or ointment may act as a coating.

Suitable composition percentages of ointment mixtures may be determined for maximal biological or healing effect. However, each of the metals listed herein may have the capability to independently form a biologically active composition at many concentrations in combination with coating materials such as organic substances. Therefore, iron filings and ferrous metal sheets that are coated with organic substances also may become biologically active and can be shaped into many different useful applications. The overall effect of the surface area involved with metallic/organic interface and the capacitance of the substance in total appears to impact (and in some aspects maximize) the biological effects.

In one aspect of the invention, an elemental metal composition may have non-linear or alternating properties (e.g., non-linear or alternating capacitance and/or field effects). In one embodiment, an elemental metal composition maybe inducible (e.g., have increasing capacitance and/or field effect upon repeated exposure to an electrostatic or electromagnetic field).

Suitable formulations may be identified and used to preserve and/or enhance the nonlinear, alternating, inducible properties of a composition of the invention. Certain formulations may be used to protect a metal from oxidation.

In some aspects, a composition of the invention may be formulated with one or more additives (e.g., preservatives, anti-bacterial, anti-inflammatory, emulsifier, thickener, hardener, etc., or any combination thereof) in addition to the elemental metal and matrix components. In some aspects, a composition may include an insulating, a corrosion resistant, and/or a hydrophobic or other water excluding material (e.g., in the form of the matrix or in addition to the matrix). The electrostatic and/or electromagnetic effects of one or more additives should be considered or assayed, and an appropriate amount should be used to prevent any unwanted effects.

It should be appreciated that a composition may include a homogeneous mixture of components (e.g., an evenly-distributed mixture). However, in some aspects, a heterogeneous mixture of components (e.g., an uneven distribution) may be effective. The distribution may be evaluated, for example, using a microscope.

In certain aspects, a composition may be provided in a container that is adapted to be contacted or exposed to an animal or plant surface. The container may be flexible, malleable, rigid, or include one or more flexible and/or malleable and/or rigid members or portions. In some aspects, a container may be a sack, bag, or other flexible container. In some aspects, an elemental metal composition of the invention may be wrapped or folded within a support material (e.g., metallic sheet, film, cloth, glass, etc.). A container may be shaped to fit onto a biological structure (e.g., anatomical feature).

A container may include one or more features adapted for attachment to a biological structure. Examples of attachment features include belts, straps, hooks, etc. Alternatively or additionally, a container may be shaped to attach to a biological structure. For example, the container may be shaped as a cylinder, sheath, glove, sock, hat, etc. In some aspects, the container may be shaped or designed to fit into an article of clothing (e.g., hat, glove, shoe, coat, etc.).

A container may be shaped as a disc or sphere (e.g., a ball). In some aspects, a composition of the invention may be shaped as a disc or sphere (e.g., a ball). For example, a disc or sphere may be between about 1 and about 5 inches in diameter. However, smaller or larger discs or spheres may be used (e.g., less than 1 inch, less than 0.5 inches, etc., or more than 1 inch, more than 5 inches, more than 10 inches, etc.). In some aspects, a disc may be about 2 inches in diameter. A disc may be of any suitable thickness. For example, a disc may be between 1/10 and 10 inches thick (e.g., about 1/8, 1/4, 3/8, 1/2, 5/8, 3/4, 7/8, 1, 5, or more inches thick). However, thinner or thicker discs may be used. It should be appreciated that many other geometric shapes may be used (e.g., squares, rectangles, triangles, cubes, etc.). It also should be appreciated that a composition of the invention may be provided in a shape that roughly approximates a geometric shape. A composition may be provided in a pad. In certain aspects, a composition may be shaped to fit an anatomical feature (e.g., of a plant or animal, for example of a human) as described in more detail herein.

In one embodiment, a container may be adapted to receive one or more biological materials. A belt or item of clothing may be adapted to receive material, with or without a surrounding container material. The material may be provided in any shape. One or more separate packages (e.g., with or without surrounding container material) may be added to a belt, an item of clothing, furniture (e.g., chair, couch, bed, car-seat), sheet, or any other suitable support. For example, 1, 2, 3, 4, 5, 6, 7, 8, 9, 10, or more packages (e.g., discs, spheres, cubes, etc.) may be affixed or introduced into a single or separate spaces or pockets in a belt, an item of clothing, furniture, sheet, or any other suitable support. In some aspects, several layers (e.g., 1, 2, 3, 4, 5, 6, 7, 8, 9, 10, or more layers) of an elemental metal composition may be separated by one or more layers of a support material (e.g., sheathing, for example fiberglass screening). In some aspects, layers of compositions may be included between layers of different materials (e.g., solid metal foil, non-conducting felt, etc., or any combination thereof) to modify the intensity of a field effect (e.g., to enhance or reduce the effect).

A container may contain dry, sticky, waxy, and/or low viscosity elemental compositions. Any suitable mass of an elemental metal composition may be used, for example, included in a container. For example, less than 1 g, 1-10 g, 10-100 g, 100-500 g, 500 g to 1 kg, 1-10 kg, 10-50 kg, or more material may be used (e.g., with or without a surrounding container).

A container may be adapted to be mixed with biological materials (e.g., a pod or small container that can be mixed with seeds or fruit or vegetables or other biological materials). A suitable storage container may be used to preserve or maintain an electrostatic charge and/or an activated state of an elemental metal composition. A container may be manufactured from any suitable material (e.g., glass, cotton, wool, silk, metals, plastics, wood, synthetic fibers, natural fibers, polymeric material, resins, etc.).

In some aspects, a container may be of a material that is untreated (e.g., that has not been treated with a chemical additive, bleaching agent, preservative, dye, paint, fire retardant or other chemical adulterant or treatment that may alter the electrostatic and/or electromagnetic properties of an elemental metal composition). For example, in some aspects, a container does not include (e.g., does not include a significant amount of, for example less than 50%, less than 40%, less than 30%, less than 20%, less than 10%, less than 5%, less than 1% by weight or volume of) a material that reduces the electronegative properties of an elemental composition (or that results in an electropositive effect). In some aspects, plastic containers (e.g., polyethylene and/or polypropylene plastic containers) are not used for medical or therapeutic (e.g., analgesic) compositions or devices of the invention. Certain containers may be used to protect a metal from oxidation. In some aspects, a container may include a desiccant. In certain aspects, a container may be air-tight and/or provide a moisture barrier.

Aspects of the invention include therapeutic applications for animals and humans as described herein. For example medical applications in human include treatments of skin conditions (e.g., psoriasis, skin cancer or pre-cancerous conditions such as hyperkeratotic lesions, melanomas, etc.). Thus, the invention also provides methods for treating a skin condition in a subject in need thereof. In general, the methods comprise exposing the subject to a low frequency, low voltage bioelectromagnetic field comprising a frequency of from about 0.1 Hz to about 20 Hz and a voltage of from about 0.1 millivolts (mV) to about 1000 mV for a period of time sufficient to treat the skin condition. In some embodiments, the period of time sufficient to treat the skin condition is at least one minute. The period of time may be several minutes, or several hours. The period of time may be spread out over a number of days, or weeks, or months, or even a year or more. Skin conditions include, but are not limited to, psoriasis, acne, dermatitis, eczema, insect bites or stings, disorders causing swelling, itching, or scaling of the skin, allergic reactions of the skin to environmental allergens, blisters, ulcers, burns, hyperkeratotic lesions, or melanomas.

Similar to methods for treating pain or inflammation, the devices and compositions suitable for use in the method of treating a skin condition, have one or more electrical properties (e.g., conductance and/or semi-conductance, inductance, resistance, capacitance, etc.) that provide beneficial electrical frequency and/or voltage responses and/or outputs when placed on or near the body of a subject. The low frequency, low voltage bioelectromagnetic field useful for the method of treating a skin condition should have a frequency and voltage in the same ranges as described hereinabove for the method of treating pain or inflammation, i.e., a frequency of from about 0.1 Hz to about 20 Hz and a voltage of from about 0.1 millivolts (mV) to about 1000 mV.

The frequency of the bioelectromagnetic field useful for the method of treating a skin condition may be from about from about 0.1 Hz to about 18 Hz, or from about 0.1 Hz to about 15 Hz, or from about 0.1 Hz to about 12 Hz, or from about 0.1 Hz to about 10 Hz, or from about 0.1 Hz to about 8 Hz, or from about 0.1 Hz to about 7.5 Hz, or from about 0.1 Hz to about 6 Hz, or from about 0.1 Hz to about 5 Hz, or from about 0.1 Hz to about 4 Hz, or from about 0.1 Hz to about 3 Hz, from about 0.1 Hz to about 2 Hz. The frequency of the bioelectromagnetic field for the method of treating a skin condition may be from about 0.5 Hz to about 20 Hz, or from about 1 Hz to about 20 Hz, from about 5 Hz to about 20 Hz, or from about 8 Hz to about 20 Hz, or from about 10 Hz to about 20 Hz, or from about 0.1 Hz to about 10 Hz, or from about 0.5 Hz to about 10 Hz, or from about 1 Hz to about 10 Hz, or from about 2 Hz to about 10 Hz, or from about 3 Hz to about 10 Hz, or from about 4 Hz to about 10 Hz, or from about 5 Hz to about 10 Hz, or from about 6 Hz to about 10 Hz, or from about 7 Hz to about 10 Hz, or from about 8 Hz to about 10 Hz.

The voltage of the bioelectromagnetic field useful for the method of treating a skin condition may be from about 0.1 millivolts (mV) to about 1000 mV, or from about 0.1 millivolts (mV) to about 800 mV, or from about 0.1 millivolts (mV) to about 600 mV, or from about 0.1 millivolts (mV) to about 500 mV, or from about 0.1 millivolts (mV) to about 400 mV, or from about 0.1 millivolts (mV) to about 250 mV, or from about 0.1 millivolts (mV) to about 200 mV, or from about 0.1 millivolts (mV) to about 100 mV, or from about 0.1 millivolts (mV) to about 75 mV from about 0.1 millivolts (mV) to about 50 mV, or from about 0.1 millivolts (mV) to about 25 mV, or from about 0.1 millivolts (mV) to about 10 mV. The voltage of the bioelectromagnetic field useful for the method of treating a skin condition may be from about 1 millivolts (mV) to about 1000 mV, or from about 10 millivolts (mV) to about 1000 mV, or from about 50 millivolts (mV) to about 1000 mV, or from about 100 millivolts (mV) to about 1000 mV, or from about 250 millivolts (mV) to about 1000 mV, or from about 500 millivolts (mV) to about 1000 mV, or from about 600 millivolts (mV) to about 1000 mV, or from about 750 millivolts (mV) to about 1000 mV, or from about 800 millivolts (mV) to about 1000 mV. Even more specifically, the without limitation, the voltage of the bioelectromagnetic field useful for the method of treating a skin condition may be from about 100 millivolts (mV) to about 750 mV, or from about 250 millivolts (mV) to about 750 mV, or from about 50 millivolts (mV) to about 500 mV, or from about 50 millivolts (mV) to about 250 mV, or from about 10 millivolts (mV) to about 100 mV, or from about 10 millivolts (mV) to about 50 mV, or from about 1 millivolts (mV) to about 100 mV, or from about 1 millivolts (mV) to about 50 mV, or from about 1 millivolts (mV) to about 25 mV.

In some preferred embodiments, the frequency of the bioelectromagnetic field useful for the method of treating a skin condition is from about 1 Hz to about 10 Hz and the voltage is from about 0.1 mV to about 500 mV. For example, the frequency may be from about 2 Hz to about 7.5 Hz and the voltage is from about 0.1 mV to about 250 mV. Furthermore, the frequency may be from about 0.5 Hz to about 4 Hz and the voltage may be from about 50 mV to about 250 mV. In some embodiments of the method of treating a skin condition, it may be beneficial, prior to bringing the device or composition into proximity or direct contact with the subject, to first determine whether the device or composition has an electrical frequency response of from about 0.01 to about 20 Hz and an electrical voltage response of from about 0.1 mV to about 1000 mV. Proximity may be less than about 10 cm, less than about 5 cm, less than about 3 cm, less than about 2 cm, less than about 1 cm, or less than about 0.5 cm.

Aspects of the invention also provide methods for treating one or more injuries (e.g., lacerations, braising, soft tissue injuries, bone fractures, burns) and pain (e.g., joint pain, neuromuscular pain, and other forms of pain). Joint or bond pain may include pain in one or more of the following: an anatomical feature, a joint, a bone, a spine or portion thereof (e.g., a foot, an ankle, a hand, a wrist, a knee, an elbow, a hip, a shoulder, a lower back region, an upper back region, a shin, a neck, etc.). Compositions of the invention may be used for similar applications in veterinary care for animals such as pets and farm animals. An animal may be a vertebrate, such as a bird, a fish, or a mammal, e.g., a mouse, cat, dog, rat, hamster, cow, pig, horse, goat, sheep, or rabbit.

In one embodiment, compositions described herein can be included with an implant or other device that is surgically inserted into a body (e.g., a human body). The composition may be coated on the surface of the implant/device or it may be encased within the body of the device or within one or more containers that are inserted into the body in proximity to the implant or device. For example, compositions of the invention may be used with implants for joint repair, non-union fracture repair, etc.

Other medical and/or veterinary uses may include: anti-pruritic; analgesic; anti-hyperplasia; anti-inflammatory; anti-infective; anti-mycotic; anti-microbial; anti-viral; anti-neoplastic; anti-proliferative; anti-psoriatic; anti-photo aging; anti-rheumatic; anti-arthritic; wound healing; augmentation of grafts and implants; inclusion in containers to preserve transplant organs; insect bite healing; treatment of warts; treatment of burns; treatment of sun burns; treatment of abrasions; treatment of ulcers; to improve healing of trauma; and/or to improve or treat any other skin condition (e.g., acne, etc.). Aspects of the invention may be used to treat inflammation, swelling and/or itching (e.g., reduce the intensity and/or duration of pain and/or itching) due to environmental, animal, or plant exposure. For example, aspects of the invention may be used to treat, prevent or reduce a response to an allergen or toxin (e.g., after exposure to animal hair or dander, pollen, animal venom, plant or animal toxin, poison ivy, poison oak etc.). Aspects of the invention may be used to treat pain or discomfort associated with a disease or condition (e.g., cancer, inflammation, tissue degeneration, injuries, fractures, arthritis, rheumatoid arthritis, osteoarthritis, a degenerative etiology of pain, a discogenic disease, etc.). In some aspects, aspects of the invention may be used to provide analgesic relief for one or more conditions. For example, analgesic relief may be provided for Osgood Schlatter's Disease, Patella-Ferneral syndrome, and/or Chondromalacia. In some aspects, compositions and devices of the invention may be used to relieve pain associated with growth (e.g., in children) or associated with tissue degeneration (e.g., associated with aging). In some aspects, compositions and devices of the invention may be used to treat regular pain (e.g., pain associated with menstrual cramps), seasonal pain or inflammation or irritation, or sporadic pain or inflammation or irritation.

In some aspects, compositions or devices described herein can be used to improve the focus or increase the alertness of a subject. Accordingly, compositions or devices described herein can be used to treat, reduce, or prevent the effects of sleep deprivation. In some aspects, compositions or devices described herein are useful to treat attention deficit disorder (ADD), attention deficit hyperactivity disorder (ADHD) or other conditions associated with reduced attention, overactivity, impulsivity, or a combination thereof. In some aspects, compositions or devices described herein can be used to treat sleep disorders, e.g., to improve sleeping patterns. In some aspects, compositions or devices described herein can be used to treat mood disorders. In some aspects, compositions or devices described herein can be used as sexual enhancement products (e.g., to increase sensation, to increase libido and/or sex drive, and/or to increase arousal and/or arousal potential).

In some aspects, compositions or devices described herein can be used to treat, prevent, or reduce one or more symptoms of a hangover (veisalgia) associated with alcohol-consumption, for example, headache, nausea, vomiting, irritation, tremor, thirst, dryness of mouth, event recall, discomfort, restlessness, impatience, or a combination thereof. For example a patch or other configuration can be applied to a subjects skin (for example on the forehead or neck) in order to prevent one or more symptoms of veisalgia. In some aspects, a patch or other configuration can be used prior to or after alcohol consumption.

Compositions or devices described herein also can be used to treat one or more of these symptoms associated with other conditions (non-alcohol related conditions) including vertigo, motion sickness, or other conditions that can cause one or more of these symptoms in a subject.

Depending on the application, the elemental metal composition may be used in a different suitable configuration (e.g., paste, cream or ointment, layered configuration, container, sheath, patch, etc.). A composition (e.g., a composition enclosed in a container) may be molded to fit an individual body part. The amount of composition that is applied may be tailored to a particular application. For example, a composition in a cream (or past or ointment) form may be applied in a sufficient amount to cover an affected area of skin or an area covering a joint or other bone or body part that is in need of treatment. If the composition is enclosed in a container, a sufficient amount should be used so that the effects of the material can reach to the desired area of treatment. The amount of material may, in part, be determined by the size of the enclosure. Accordingly, different amounts of material may be used (e.g., from several grams to several kilograms, for example, about 5 g, 10 g, 20 g, 30 g, 40 g, 50 g, 100 g, 250 g, 500 g, or 750 g). However, smaller or larger amounts may be used. Similarly, the duration of exposure may be tailored to a particular application and also may be determined by the user. For example, if a desired result is obtained (e.g., pain relief) a subject may discontinue use. In other aspects, a subject may be exposed on a regular basis (e.g., every day, once a week, etc.) to a suitable composition. In one embodiment, a subject may be exposed at night. For example, a suitable composition may be applied at night or incorporated into a bedding material (e.g., a pillow, blanket, mattress, other suitable enclosure, an animal bedding material, etc.). In addition, or alternatively, a subject may be exposed during the day. For example, a suitable composition may be included in clothing material (e.g., pants, shirts, skirts, coats, gloves, hats, shoes, socks, etc.). In one embodiment, a composition may be provided in an enclosure that can be attached to, or placed in, an item of clothing (e.g., in a hat, glove, shoe, pocket, etc.).

In other aspects, a composition of the invention may be included in a bandage (e.g., included in a pad in a bandage such as a band-aid) or other material that is used to wrap or cover a wound or painful area of a body.

In certain aspects, a composition may be formed into one or more separate shapes that can be inserted into container, a pocket, or sewn into a belt or other support. For example, a belt may include one or more discs of material (e.g., 1-5, 5-10, or more).

An animal surface (e.g., skin) may be exposed to a composition of the invention directly or indirectly (e.g., in a container or through clothing, bedding, or furniture) for any suitable period of time (e.g., 1-5, 5-10, 10-30, or longer), one or more hours (e.g., 1-5, 5-10, or longer), one or more days (e.g., 1, 2, 3, 4, 5, 6, 7, 8, 9, 10, or more), one or more weeks (e.g., 1, 2, 3, 4, 5, 6, 7, 8, 9, 10, or more), one or more months (e.g., 1-5, 5-10, or longer) or one or more years (e.g., 1, 2, 3, 4, 5, etc.). In some aspects, an animal may be exposed to an elemental metal material on a regular and/or seasonal basis (e.g., every, spring, summer, fall, winter, or any combination thereof) depending on the application and/or the condition being treated.

Aspects of the invention also include plant applications. Compositions or devices of the invention may be used to alter one or more aspects of plant physiology (germination, growth, flowering, ripening, decaying, etc.). Compositions of the invention may be used in connection with any plant tissue, including, but not limited to, seeds, roots, branches, fruits, vegetables, etc. In some aspects, a composition of the invention may be applied directly to plant material (e.g., in the form of a cream, oil, or other similar substance). In other aspects, a composition of the invention may be provided in a container or sheath that can be contacted with plant tissue, structure, or cells (e.g., roots, stems, branches, leaves, seeds, flowers, etc.). For example, a composition of the invention may be provided in bags or solid containers that can be included with seeds (e.g., in seed silos, sacs, etc.) in order to enhance germination (e.g., to speed up germination, to increase the percentage of seeds that germinate, etc., or any combination thereof). In one embodiment, seeds may be stored with a device of the invention. In another embodiment, a device of the invention may be added to seed containers when germination is desired (or for example several weeks prior to germination or before seeds are sowed). In one embodiment, seeds may be coated directly with a composition of the invention. A composition of the invention may be used as a seed or soil "amendment." In one embodiment, one or more elemental metals (e.g., particulate elemental metals) that may be coated (e.g., with a non-conducting or semi-conducting material) or non-coated may be added to an existing seed or soil "amendment" that contains one or more other active ingredients. In one embodiment, a container or surface (e.g., a table) may include one or more layers of coated elemental metal(s) of the invention (e.g., 2, 3, 4, 5, 6, 7, 8, 9, 10, or more layers). Plant material (e.g., bulbs, seeds, seedlings, small plants, large plants, vegetables, fruit, etc.) then may be contacted with the biologically active composition by putting the plant material in the container, on the table, or near any other suitable device that contains a biologically active composition of the invention. In yet other aspects, a device (e.g., a weather resistant device) may be placed on or near a plant growing inside (e.g., in a house or a greenhouse) or outside (e.g., in a garden, field, or forest) or in water (e.g., in a tank, pond, lake, river, sea, ocean, etc.).

In other aspects, an elemental metal composition of the invention may be added, either directly or in a suitable container, to agricultural/horticultural products such as soil (e.g., top-soil), mulch, fertilizer, insect or other pest control compositions, etc. In some aspects, an elemental metal composition of the invention may be applied to the inner surface of a container (e.g., a vial, beaker, vase, vat, silo, etc., or any combination thereof) that will be used to store, germinate, and/or grow seeds and/or other plant material. In some aspects, a formulation of the invention may be included in a seed tray, a growing platform, or other surface or container. In some aspects, a composition of the invention may be covered or contained within a material that does not reduce the electro-negative properties of the material or result in an electro-positive environment. In some aspects, plastic (e.g., polyethylene and/or polypropylene plastic) is not used as a coating or encasing material.

In some aspects, a composition for use with a plant may include one or more elemental metals that are plant nutrients (e.g., micro- or macro-nutrients essential for plant growth). Examples of macronutrients include: N, K, Ca, Mg, P, and S. Examples of micronutrients include: Cl, Fe, B, Mn, Zn, Cu, Mo, and Ni.

Accordingly, aspects of the invention may be used to improve food storage and/or transport; to improve seed and/or grain germination; or to improve fruit, grain and/or seed yield. Aspects of the invention may be used in connection with any plant or seed, for example any agricultural plant or seed (e.g., barley, corn, cotton, rice, soy, wheat, lettuce, tomatoes, potatoes, apples, oranges, pairs, bananas, etc.) or any flower plant or seed.

As described above for medical applications, large or small amounts of material may be used and may be exposed to plant material for relatively short or long periods of time depending on the application and the desired result. In some aspects, a seed or plant may be exposed to an elemental metal composition for one or more minutes (e.g., 1-5, 5-10, 10-30, or longer), one or more hours (e.g., 1-5, 5-10, or longer), one or more days (e.g., 1, 2, 3, 4, 5, 6, 7, 8, 9, 10, or more), one or more weeks (e.g., 1, 2, 3, 4, 5, 6, 7, 8, 9, 10, or more), one or more months (e.g., 1-5, 5-10, or longer) or one or more years (e.g., 1, 2, 3, 4, 5, etc.). In some aspects, a seed or plant may be exposed to an elemental metal material on a regular and/or seasonal basis (e.g., every, spring, summer, fall, winter, or any combination thereof).

It should be appreciated that suitable amounts of material and/or durations of exposure may be optimized by comparing results for animals or plants exposed to different amounts (e.g., including a placebo control), and/or durations of one or more different types of elemental metal compositions with or without containers (e.g., using one or more different types of containers). The effectiveness of an exposure may be evaluated statistically. In some aspects, an exposure of the invention (e.g., a combination of type and amount of material, container, and/or duration or exposure) is designed to be an amount sufficient to have a statistically significant effect. In some aspects, the effectiveness of a therapeutic composition may be evaluated in a double-blind placebo-controlled trial. In some aspects, the effectiveness to treat pain or inflammation may be evaluated by obtaining average patient reports (e.g., using a pain scale, for example a 0-10 Lickert type scale) relative to a control on a daily, weekly, monthly, or other time-dependent basis and evaluating them using one or more statistical tests. In some aspects, a patient quality of life score (e.g., related to activity and/or mobility) may be used to evaluate effectiveness. In some aspects, the average amount of medication used over a certain time period (e.g., a week, a month, or longer) may be evaluated to determine if a treatment is effective.

It should be appreciated that for medical, veterinary, and/or plant uses, a composition of the invention may be combined with one or more other compositions or preparations that are used to treat or enhance an animal or plant biological process. In some aspects, a composition of the invention may be sterilized. In one embodiment, a composition may be prepared from sterile materials. In one embodiment, a composition may be sterilized after preparation or during preparation (e.g., by heating, irradiation, etc.).

It should be appreciated that in some aspects, a composition of the invention may have a limited period of effectiveness (e.g., a period during which a useful electronegative or electropositive effect is maintained). Accordingly, certain compositions of the invention may be disposable an or rechargeable. For example, an elemental metal composition may be rechargeable as described herein. In some aspects, a container described herein may be refillable (e.g., with freshly produced or recycled elemental metal material).

It also should be appreciated that compositions of the invention may be useful to alter growth, differentiation, or other properties of biological materials ex vivo or in vivo (e.g., to enhance plant, animal, or microbial cell growth in vitro, to preserve organs such as organs for transplantation, to preserve plants or plant grafts for transport, etc.).

The following examples are provided to describe the invention in greater detail. They are intended to illustrate, not to limit, the invention.

EXAMPLE 1

Bioelectromagnetic Fields Effectively Treat Pain, Inflammation, Itching, and Acne Different compositions were tested for their effectiveness to treat different conditions, including different sources of pain, inflammation, itching, and acne as shown in Table 1. Compositions were contacted directly to the skin of a subject, or were enclosed within a container (e.g., a wrap) such that the compositions did not contact the skin directly. Different types of elemental metals were used including combinations of one or more of iron, aluminum, copper, zinc, stainless steel, nickel, bronze, silver, gold, cobalt, or selenium, mixed with one or more of bees wax, lanolin, silicone, silicone powder, silicone adhesive, hydrocolloid, PTFE, castor oil, petroleum jelly, candle wax, polyethylene, mineral oil, or sulfur contained within wraps, including fixation devices and belts made from natural fabrics (such as wool, cotton, and silk), synthetic fabrics (such as synthetic polymers and neoprene), and commercial dressings and commercial adhesives shaped to fit the body part being treated. Representative results are shown in Table 1.

TABLE 1

| Prototype variation number | Clinical Indication Tested | Clinical Result- effects decrease pain unless otherwise described* | Length of Exposure | Confirm 5 point scale improvement |
|---|---|---|---|---|
| 1 | Joint Sprain | 2 patients +1/5 | | |
| 3 | Joint Sprain | 2 patients +1/5 | | |
| 4 | Joint Sprain | 2 patients +1/5 | | |
| 6 | Joint Sprain, Tension H/A | 2 patients, each +0/5 | | |
| 8 | Joint Sprain, Lymphoma Pain & Fatigue | 3 patients, each +2/5, 1 canine +2/5 | | |
| 21 | Joint Sprain | 3 patients +1/5 | | |
| 22 | Joint Sprain | 3 patients +2/5 | | |
| 23 | Joint Sprain | 3 patients +3/5 | | |
| 24 | Joint Sprain | 3 patients +1/5 | | |
| 27 | Joint Sprain | 3 patients +2/5 | | |
| 29 | Joint Sprain, Tension H/A | 2 patients JS +1/5, HA +2/5 | | |
| 31 | Tension H/A | 1 patient 0/5 | | |
| 35 | Joint Sprain | 1 patient 0/5 | | |
| 36 | Joint Sprain | 1 patient 0/5 | | |
| 37 | Joint Sprain, Tension H/A, Discogenic Dz, Low-Back Sprain-Strain, Osteoarthritis | 10 patients +1/5 | | |
| 38 | Joint Sprain, Tension H/A, Discogenic Dz, Low-Back Sprain-Strain | 5 patients +1/5 | | |
| 39 | Joint Sprain, Tension H/A, Discogenic Dz, | 5 patients +2/5 | | |

TABLE 1-continued

| Prototype variation number | Clinical Indication Tested | Clinical Result- effects decrease pain unless otherwise described* | Length of Exposure | Confirm 5 point scale improvement |
|---|---|---|---|---|
| 40 | Low-Back Sprain-Strain Joint Sprain, Tension H/A, Discogenic Dz, Low-Back Sprain-Strain | 5 patients +1/5 | | |
| 42 | Joint Sprain, Tension H/A, Discogenic Dz, Low-Back Sprain-Strain | 3 patients +1/5 | | |
| 43 | Joint Sprain, Tension H/A, Psoriasis, Hyperkeratosis | 5 patients +3/5, diminished psoriasis 1 patient +3/5 | 1-10 hours | Confirmed Improvement |
| 44 | Joint Sprain, Tension H/A, Discogenic Dz, Low-Back Sprain-Strain, Psoriasis, Hyperkeratosis, Acne | 5 patients pain +3/5, skin conditions decrease +2/5 | 1-10 hours | Confirmed Improvement |
| 45 | Joint Sprain, Tension H/A, Discogenic Dz, Low-Back Sprain-Strain, Psoriasis, Hyperkeratosis, Acne | 5 patients pain +3/5, skin conditions decrease +3/5 | 1-10 hours | Confirmed Improvement |
| 46 | Joint Sprain, Tension H/A, Discogenic Dz, Low-Back Sprain-Strain, Psoriasis | 10 patients pain +3/5, skin conditions +2/5 | 1-10 hours | Confirmed Improvement |
| 47 | Lymphoma Pain & Fatigue | Canine +1/5 | 1-10 hours | Confirmed Improvement |
| 48 | Lymphoma Pain & Fatigue | Canine +3/5 | 1-10 hours | Confirmed Improvement |
| 49 | Joint Sprain, Tension H/A, Discogenic Dz, Low-Back Sprain-Strain, Osetoarthritis, Psoriasis, Hyperkeratosis, Acne | 5 patients pain +3/5, skin conditions +3/5 | 1-10 hours | Confirmed Improvement |
| 50 | Joint Sprain, Tension H/A | 3 patients +3/5, HA +1/5 | 1-10 hours | Confirmed Improvement |
| 51 | Joint Sprain, Tension H/A, Psoriasis, Hyperkeratosis | 3 patients +2/5, skin conditions +1/5 | 1-10 hours | Confirmed Improvement |
| 52 | Psoriasis | 1 patient decrease +2/5 | 1-10 hours | Confirmed Improvement |
| 53 | Tension H/A, Discogenic Dz, Low-Back Sprain-Strain, Bum Pain, Psoriasis | 5 patients +3/5 | 1-10 hours | Confirmed Improvement |
| 55 | Tension H/A, Psoriasis | 2 patients H/A +1/5, skin +2/5 | 1-10 hours | Confirmed Improvement |
| 56 | Tension H/A, Metastatic bone and soft tissue cancer pain, Lymphoma pain | 2 patients H/A +1/5, 4 CA patients +5/5, 1 Canine +5/5 | 1-10 hours | Confirmed Improvement |
| 57 | Joint Sprain | 2 patients +3/5 | 1-10 hours | Confirmed Improvement |
| 60 | Joint Sprain | 5 patients +2/5 | 1-10 hours | Confirmed Improvement |
| 61 | Joint Sprain, Tension H/A, Bum Pain, Psoriasis | 20 patients +5/5, skin +3/5 | 1-10 hours | Confirmed Improvement |

TABLE 1-continued

| Prototype variation number | Clinical Indication Tested | Clinical Result-effects decrease pain unless otherwise described* | Length of Exposure | Confirm 5 point scale improvement |
|---|---|---|---|---|
| 62 | Joint Sprain | 1 patient +1/5 | 1-10 hours | Confirmed Improvement |
| 63 | Joint Sprain | 1 patient +1/5 | 1-10 hours | Confirmed Improvement |
| 67 | Joint Sprain, Tension H/A, Migraine H/A, Dental & TMJ Pain, Neck Sprain, Neuralgia, Discogenic Dz, Low-Back Sprain-Strain, Osteoarthritis, Plantar Fasciitus, Turf Toe, Tendonitis, Patella-Femoral Syndrome, Compartment Syndrome, Chronic Lower Back Pain, Menstrual Cramps, Post-surgical Pain | 30 patients +4-5/5 | 1-10 hours | Confirmed Improvement |
| 71 | Joint Sprain, Tension H/A, Migraine H/A, Dental & TMJ Pain, Neck Sprain, Neuralgia, Discogenic Dz, Low-Back Sprain-Strain, Osteoarthritis, Osteochondritis Dessicans, Plantar Fasciitus, Shin Splints, Stress Fracture, Turf Toe, Fracture Pain, Achilles tendon rupture, Tendonitis, Cancer Pain, Lymphoma Pain & Fatigue, Carpal Tunnel Syndrome, Patella-Femoral Syndrome, Compartment Syndrome, Chronic Lower Back Pain, Burn Pain, Menstrual Cramps, Sinusitis, Incisional Pain, Post-surgical Pain, Psoriasis, Hyperkeratosis, Acne | Double Blind Placebo Controlled Back Pain clinical trial (37 patients-see Clinical Study report). At least 60 additional patients for other various syndromes listed: results +5/5 | 1-10 hours | Confirmed Improvement |
| 72 | Joint Sprain, Tension H/A, Migraine H/A, Dental & TMJ Pain, Neck Sprain, Neuralgia, Discogenic Dz, Low-Back Sprain-Strain, Osteoarthritis, Plantar Fasciitus, Shin Splints, Stress Fracture, Turf Toe, Fracture Pain, Achilles tendon rupture, Tendonitis, Cancer Pain, Lymphoma Pain & | 30 patients +4/5 | 1-10 hours | Confirmed Improvement |

TABLE 1-continued

| Prototype variation number | Clinical Indication Tested | Clinical Result- effects decrease pain unless otherwise described* | Length of Exposure | Confirm 5 point scale improvement |
|---|---|---|---|---|
| | Fatigue, Carpal Tunnel Syndrome, Patella-Femoral Syndrome, Compartment Syndrome, Chronic Lower Back Pain, Burn Pain, Menstrual Cramps, Sinusitis, Incisional Pain, Post-surgical Pain, Psoriasis, Hyperkeratosis, Acne | | | |
| 73 | Joint Sprain | 3 patients +2/5 | 1-10 hours | Confirmed Improvement |
| 74 | Joint Sprain | 3 patients +2/5 | 1-10 hours | Confirmed Improvement |
| 75 | Joint Sprain, Tension H/A, Discogenic Dz, Low-Back Sprain-Strain, Osteoarthritis, Plantar Fasciitus, Shin Splints, Tendonitis, Patella-Femoral Syndrome, Chronic Lower Back Pain, Menstrual Cramps, Incisional Pain | 20 patients +5/5 | 1-10 hours | Confirmed Improvement |
| 77 | Psoriasis | 1 patient +2/5 | 1-10 hours | Confirmed Improvement |
| 78 | Joint Sprain, Tension H/A, Migraine H/A, Dental & TMJ Pain, Neck Sprain, Neuralgia, Discogenic Dz, Low-Back Sprain-Strain, Osteoarthritis, Plantar Fasciitus, Shin Splints, Stress Fracture, Turf Toe, Fracture Pain, Achilles tendon rupture, Tendonitis, Cancer pain, Lymphoma Pain & Fatigue, Carpal Tunnel Syndrome, Patella-Femoral Syndrome, Compartment Syndrome, Chronic Lower Back Pain, Burn Pain, Menstrual Cramps, Sinusitis, Incisional Pain, Post-Surgical Pain, Psoriasis, Hyperkeratosis, Acne | 20 patients +3/5 | 1-10 hours | Confirmed Improvement |
| 79 | Joint Sprain, Tension H/A, Migraine T/A, Dental & TMJ Pain, Neck Sprain, Neuralgia, Discogenic Dz, Low-Back Sprain-Strain, | 30 patients +5/5 | 1-10 hours | Confirmed Improvement |

TABLE 1-continued

| Prototype variation number | Clinical Indication Tested | Clinical Result- effects decrease pain unless otherwise described* | Length of Exposure | Confirm 5 point scale improvement |
|---|---|---|---|---|
|  | Osteoarthritis, Plantar Fasciitis, Shin Splints, Stress Fracture, Turf Toe, Tendonitis, Carpal Tunnel Syndrome, Patella-Femoral Syndrome, Chronic Lower Back Pain, Menstrual Cramps, Incision Pain, Post-surgical Pain |  |  |  |
| 80 | Chronic Low back pain, Neck Pain, Shoulder Pain, Muscle Spasm, Acne, Insect bite-inflammation & Itch | 4 patients +5/5 Decreased Skin Inflammation +3/5; Decreased itch +5/5 | 1-10 hours | Confirmed Improvement |

In Table 1: *Maximal recorded pain reduction response on 5 point scale; 0 = no reduction in pain, +1 = mild reduction, +2 = mild to moderate reduction, +3 = moderate reduction, +4 = significant reduction, +5 = complete relief of pain.

EXAMPLE 2

Measurement of Electromagnetic Fields

One or more physical properties of a composition or device described herein (e.g., capacitance; electrostatic field effect; electromagnetic field effect; charge; etc.) can be measured using any suitable method. Measured physical properties can be used to evaluate biological effectiveness and determine which application(s) a composition or device may be suited for. In addition, the measured physical properties of a composition or device may be used to determine how to modify a composition to change its physical properties and adapt it for a particular biological application.

In some aspects, the disclosure relates to techniques for evaluating or quantifying the electrical properties of a device or composition that is to be used for producing a biological field effect when placed in proximity to (or on) the skin of a subject.

In some aspects, a Kolbe Electroscope is negatively charged to a stable midrange. A material to be tested is charged by exposure to a suitable energy source (e.g., by exposure to sunlight, to negative ions from a negative ion generator, to a Van de Graff generator, to a body surface, or to any other suitable energy source). The charged material is then brought within the field of the charged Kolbe electroscope and the response is measured. A negative field response is shown by a drop of the charged electroscope, no response is shown by no change or drop in the charged electroscope, a low response is shown by a small deflecting increase <1 segment response, a moderate response is shown by a 1 segment increase in charge, and a high response is shown by a >1 segment increase.

Figure 1B:
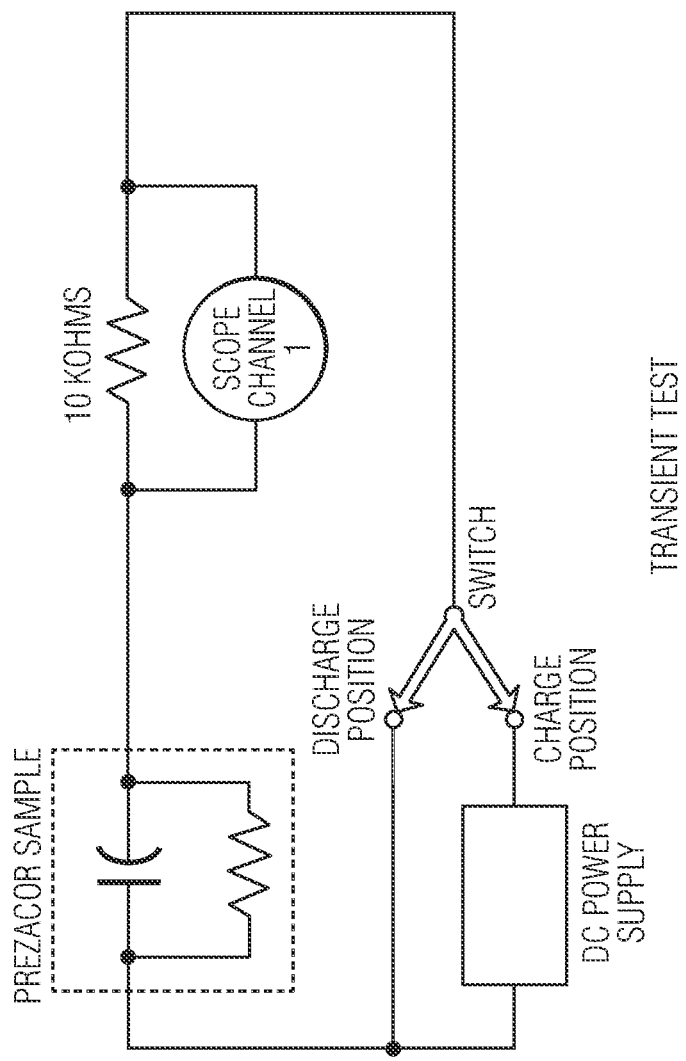
Figure 1C:
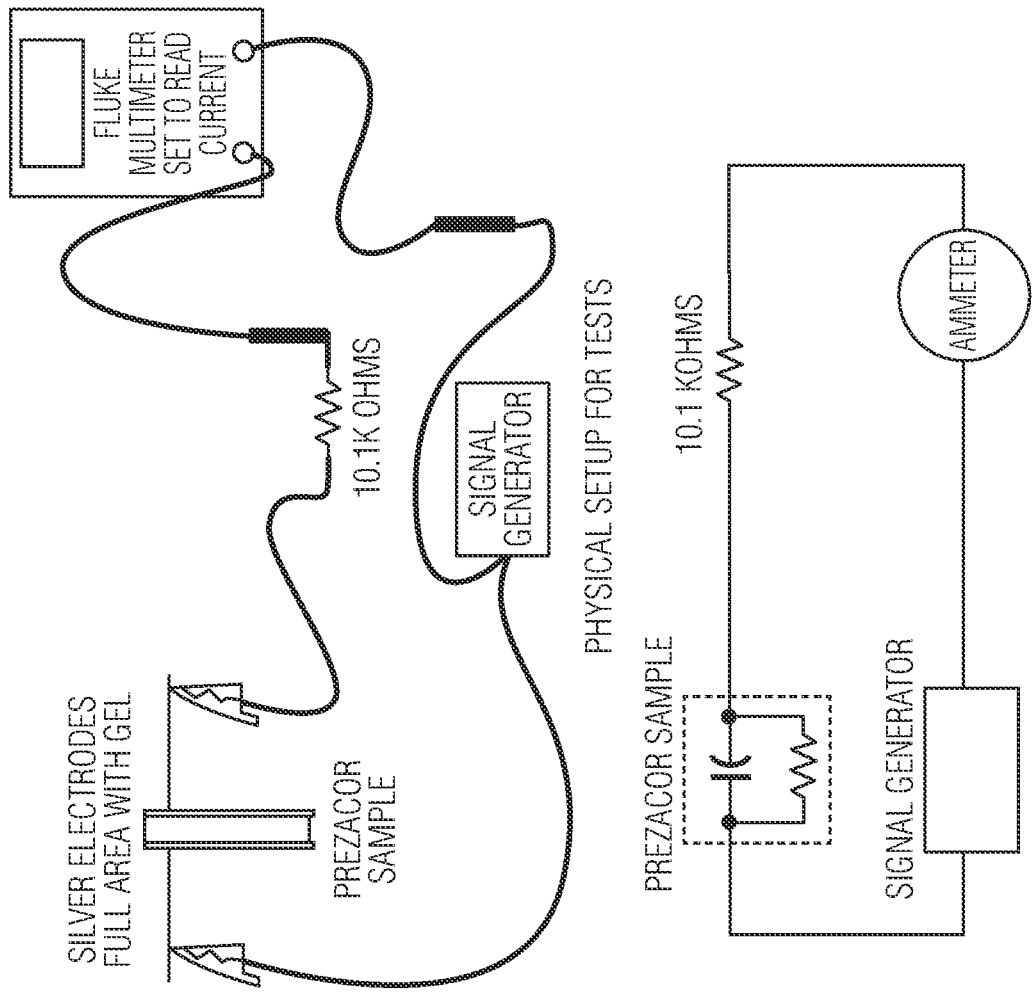

In some aspects, one or more non-limiting circuit configurations illustrated in FIGS. 1A-1C can be used. FIG. 1A illustrates a non-limiting embodiment of a circuit that can be used to evaluate (e.g., measure) a phase shift between applied voltage and current flow caused by a composition or device being tested. This can be used to evaluate the energy storage functionality of a composition or device. Phase shifts can be tested at different frequencies such as those described herein. FIG. 1B illustrates a non-limiting embodiment of a circuit that can be used to evaluate (e.g., measure) a transient discharge resulting from the storage of electromagnetic energy by a composition or device described herein. FIG. 1C illustrates a non-limiting embodiment of a circuit that can be used to evaluate (e.g., measure) current in a composition or device described herein (e.g., at one or more different frequencies described herein).

In addition to the aspects of the invention described above, additional variations are contemplated. For example, certain exemplary embodiments of the invention relate to a monopolar pain relief device. More specifically, an exemplary pain relief device includes (i) a body portion including a contact region configured for contacting a subject, and (ii) a monopolar transmitter (which may be, for example, a distinct monopolar transmitter, or part of an integrated monopolar transceiver) including a single electrical pole for providing an electrical signal to the body portion for treatment of the subject (e.g., where the subject may be a human patient, a non-human patient such as a pet or other animal, etc.). Depending on the specific design, the contact region of the body portion may be considered to be electrically equivalent to the single pole of the monopolar transmitter. Throughout the description set forth below, certain elements shall be referred to as a monopolar transmitter; however, it is understood such an element may be a monopolar transmitter, a monopolar transmitter along with a monopolar receiver, or a monopolar transceiver.

Referring to the body portion of such a monopolar pain relief device, the body portion may include, and/or be one of, a variety of medical devices. For example, the body portion may be a patch, a sleeve, a garment, etc. Additional exemplary medical devices are described below with respect to FIGS. 5A-5K. The contact region of the body portion may be formed from an electrically conductive material. In addition to the function of providing electrical signals from the monopolar transmitter for treatment of a subject (e.g., where the electrical signals may be provided through a surface electricity at the interface between the monopolar transmitter and the subject), the body portion of the pain relief device may also be configured to receive electrical signals from the subject (e.g., through the single pole of the monopolar transmitter, where the electrical signals may be provided through a surface electricity at the interface between the monopolar transmitter and the subject). Thus, as opposed to a multi-pole transmitter for generating and transmitting electrical signals to the subject, the monopolar transmitter interacts with the subject causing electrical signals to be transferred (i) from the monopolar transmitter to the subject, and/or (ii) from the subject to the monopolar transmitter, in the treatment of the subject.

The pain relief device may include a signal generator (e.g., such as a waveform generator), for example, which may be included in a programmable device of the pain relief device. The signal generator may generate the electrical signal (for treating the subject) to have a frequency between, for example: 0.1 Hz and 20 Hz; 0.1 Hz and 10 Hz; and 0.1 Hz and 5 Hz. The signal generator may generate the electrical signal (for treating the subject) to have a voltage between, for example: 0.1 volts and 10 volts; 0.1 volts and 5 volts; and 0.1 volts and 1 volt.

As provided above, the pain relief device may include a programmable device. Such a programmable device may include computer program instructions for providing treatment options for use by the subject. For example, the treatment options may be customized based on patient criteria of the subject. Examples of such patient criteria include at least one of an age of the subject, a gender of the subject, and feedback from the subject regarding prior treatment.

The electrical signals transmitted from the pain relief device to the subject utilize the single electrical pole of the monopolar transmitter to interact with the subject. In certain examples, the single electrical pole of the monopolar transmitter may be considered a form of antenna. In a further example, the second electrical "pole" may be insulated from the subject such that the electrical circuit between the subject may include a path through the "air", or "ground", or "earth".

Further, as will be explained in greater detail below, the monopolar transmitter (which may include a receiver, and/or which may be a transceiver) may be used to measure waveforms/electrical signals on the surface of the human body. For example, such waveforms/signals may be naturally occurring on the surface of the human body. In another example, such waveforms/signals may be in response to treatment (e.g., from the monopolar transmitter). Such waveforms/signals may be associated with pain, or may not be associated with pain. The waveforms/signals may be acquired (e.g., using a data acquisition function) where the waveforms/signals may be analyzed, processed, and/or reformulated to determine a treatment to be applied to the subject, among other functions. Further, aspects of the invention involve a mass data acquisition process that may have wide implications to the study of energy medicine to many pathologies in addition to the application and treatment of pain (analgesia).

Figure 3B:
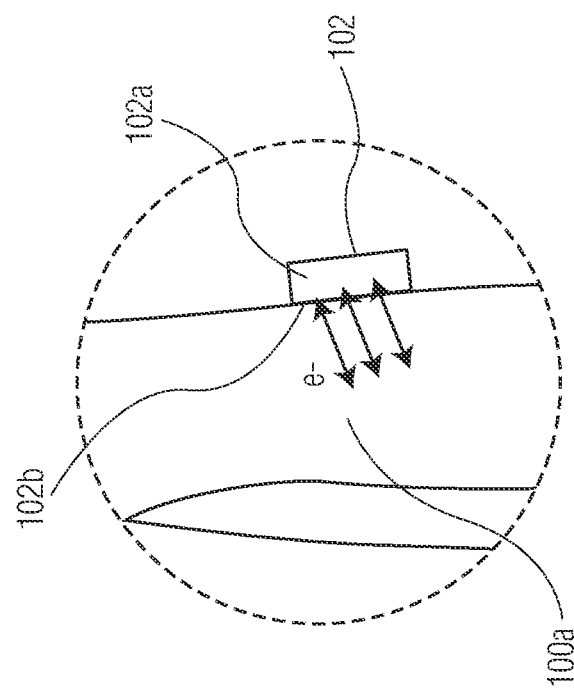
FIG. 3B is a detailed view of a portion of FIG. 3A.
Figure 3A:
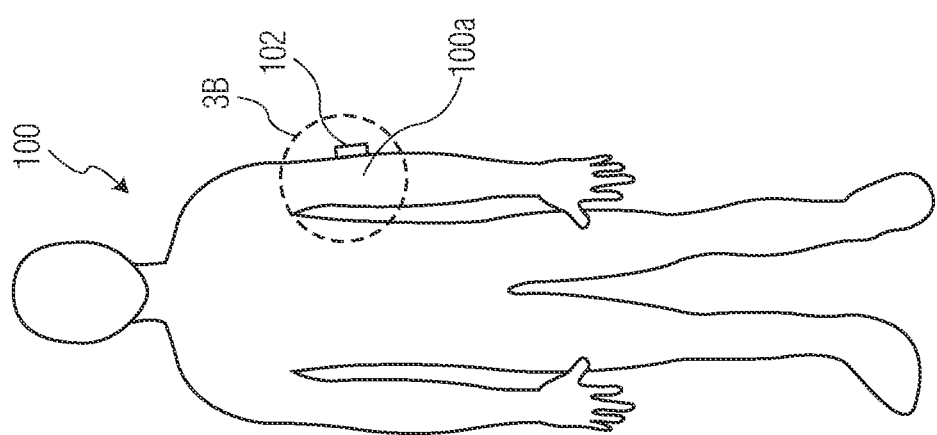
FIG. 3A is a drawing of a subject using a pain relief device in accordance with an exemplary embodiment of the invention.

Referring now to FIG. 3A, a subject 100 (e.g., a human patient) is shown using a pain relief device 102 for treatment of a site of discomfort 100*a* (e.g., an injured elbow). That is, in FIG. 3A, pain relief device 102 is a form of medical patch/pad secured to the elbow of subject 100 (in this example, the site of discomfort 100*a* is the elbow). FIG. 3B is a closer view of pain relief device 102 secured to site 100*a* through contact region 102*b* of pain relief device 102. Electrical signals (illustrated as "e-" in FIG. 3B) are transferred between pain relief device 102 and the site of discomfort 100*a* of subject 100.

Figure 3C:
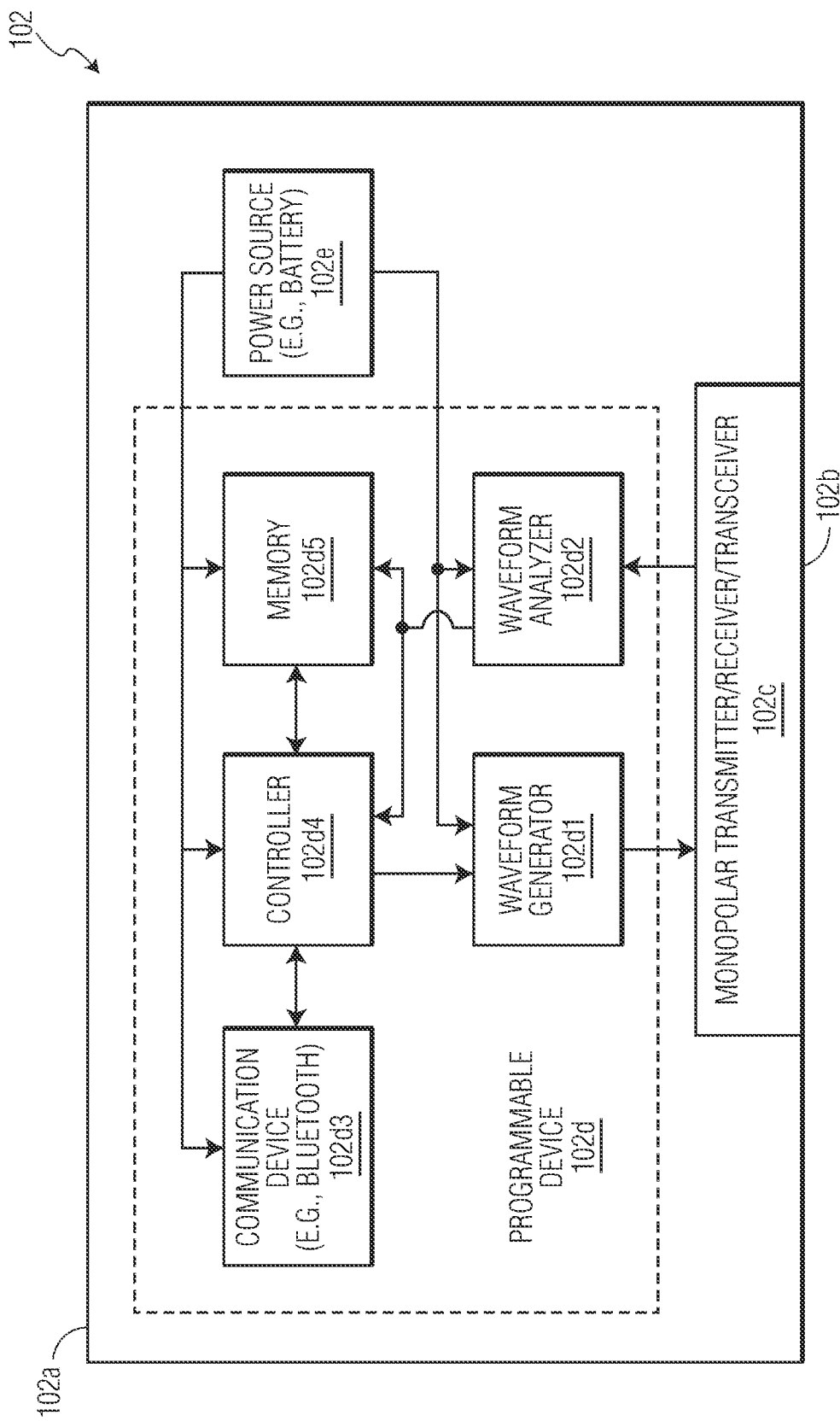
FIG. 3C is a block diagram view of a pain relief device in accordance with an exemplary embodiment of the invention.

FIG. 3C is a block diagram of an exemplary pain relief device 102 including body portion 102*a*. As will be appreciated by those skilled in the art, pain relief device 102, as shown in FIG. 3C, has a simplistic shape for ease of illustration; however, pain relief device 102 may have any shape desired for the given application (e.g., a patch as shown in FIGS. 3A-3B, any of the shapes of the devices 502*a*-502*k* shown in FIGS. 5A-5K, among others).

Still referring to FIG. 3C, pain relief device 102 includes contact portion 102*b*. In this example, contact portion 102*b* is adjacent monopolar transmitter 102*c* including a single pole (which may also include a receiver for receiving electrical signals, and/or may be a monopolar transceiver 102*c*). Exemplary pain relief device 102 also includes a programmable device 102*d* and a power source 102*e* (e.g., a battery). Power source 102*e* provides electrical power for the various elements of programmable device 102*d* including waveform generator 102*d*1, waveform analyzer 102*d*2 (e.g., providing a spectrum analyzer function, such as through the use of an oscilloscope), communication device 102*d*3, controller 102*d*4, and memory 102*d*5. Programmable device 102*d* (e.g., through controller 102*d*4 and/or memory 102*d*5) includes computer program instructions for providing treatment options for use by subject 100. An exemplary operation of the elements of programmable device 102*d* will now be described.

Controller 102*d*4 has access to treatment instructions for subject 100. For example, the treatment instructions may be stored in memory 102*d*5, and the treatment instructions may be accessed by controller 102*d*4. In another example, the treatment instructions may be provided via communication device 102*d*3 in communication with a user device (e.g., a bluetooth device, such as a smart phone or other device, etc.). In yet another example, the treatment instructions may be determined by controller 102*d*4, for example, using data from waveform analyzer 102*d*2. Further still, combinations of these examples are contemplated (e.g., where initial treatment instructions may be provided via a user device, and then may be updated using the data from waveform analyzer 102*d*2.

Regardless of the origin of the treatment instructions, controller 102*d*4 controls waveform generator 102*d*1 to provide electrical signals to monopolar transmitter 102*c* for transmission of electrical signals to subject 100 (e.g., for treatment of subject 100). Signals from monopolar transmitter 102*c* (e.g., where such signals may represent a status/characteristic of subject 100 wearing the pain relief device 102) may be received by waveform analyzer 102*d*2, where output signals from waveform analyzer 102*d*2 (related to the signals from monopolar transmitter 102*c*) are provided to at least one of controller 102*d*4 and memory 102*d*5 (where memory 102*d*5 may store information from waveform analyzer 102*d*2 for later analysis and treatment determination). Such signals from waveform analyzer 102*d*2 may be used by controller 102*d*4 in determining a present, or future treatment to be provided to the subject. That is, controller 102*d*4 may be used to provide treatment signals through waveform generator 102*d*1 in a closed loop manner, with an input to the closed loop being data/measurements collected from the subject using waveform analyzer 102*d*2. Specifically, waveform analyzer 102*d*2 and controller 102*d*4 may be used in a closed loop manner to efficiently provide pain relief (e.g., maximized pain relief) in real time by measuring the subject steady state and response to treatment.

Figure 4B:
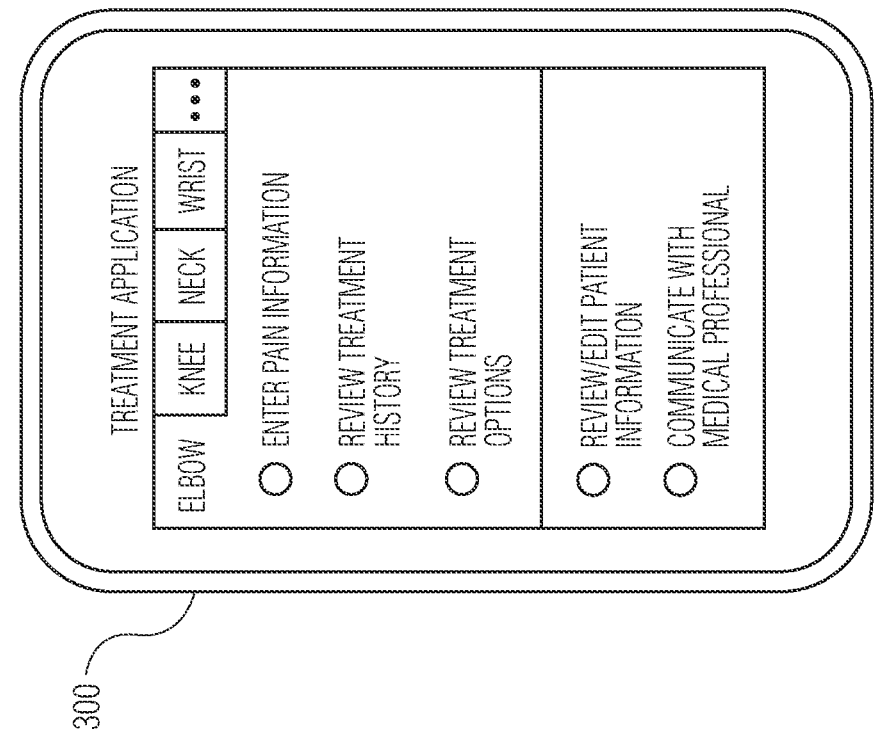
FIG. 4B is a block diagram illustration of the user device of FIG. 4A, running a software application on the user device, in accordance with an exemplary embodiment of the invention.
Figure 4A:
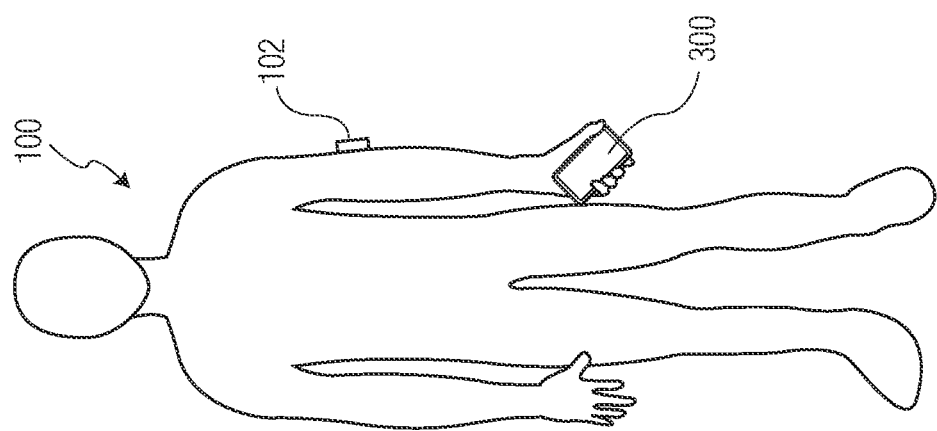
FIG. 4A is a drawing of a subject using a pain relief device in connection with a user device, in accordance with an exemplary embodiment of the invention.

FIG. 4A illustrates subject 100 holding a personal electronic device 300 (e.g., sometimes referred to as a user device, with exemplary user devices being a cell phone, a smart phone, a tablet, etc.). User device 300 may be used (e.g., by subject 100) in communication with pain relief device 102. For example, user device 300 may be bluetooth enabled, and may communicate with pain relief device 102 via communication device 102d3 of programmable device 102d. Bluetooth communication is just one exemplary method of communication between user device 300 and communication device 102d3. Other wired, and/or wireless, communication methods are contemplated.

FIG. 4B illustrates user device 300 with a user interface of an exemplary software treatment application shown on the screen of user device 300. It will be understood that the details of the software treatment application shown on the screen of user device 300 is just one example, and the user interface (and the functionality of the software treatment application) may vary within the scope of the invention. The user interface in FIG. 4B illustrates a series of body parts which may now (or in the future) experience discomfort, such that subject 100 (or another person, such as a medical professional) may select the "tab" corresponding to the appropriate body part (e.g., elbow, knee, neck, wrist, etc.). The user (e.g., subject 100) may (i) enter pain information about the body part, (ii) review the treatment history associated with the body part, and/or (iii) review treatment options for the body part. The user may also review/edit the patient information (e.g., age, gender, medical details, family history, etc.), and/or may communicate with a medical professional, etc. Of course, other functions may be available to a user of user device 300 in connection with communication between user device 300 and pain relief device 102.

Figure 5C:
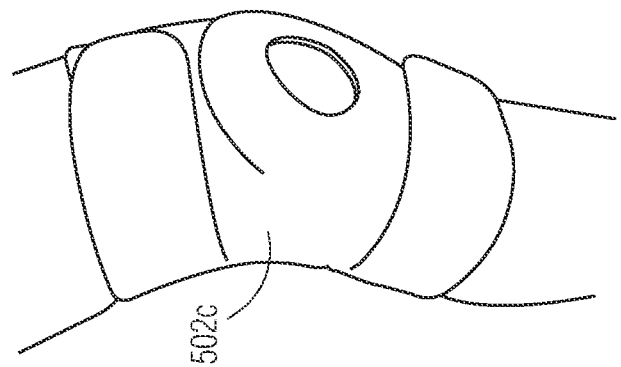
FIGS. 5A-5K are illustrations of various pain relief devices worn by subjects in accordance with various exemplary embodiments of the invention.
Figure 5B:
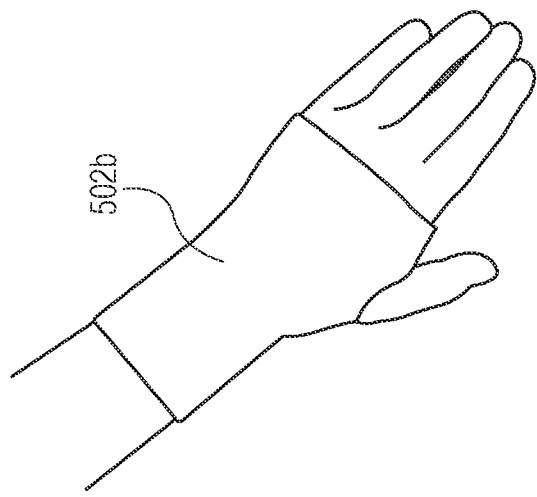
Figure 5A:
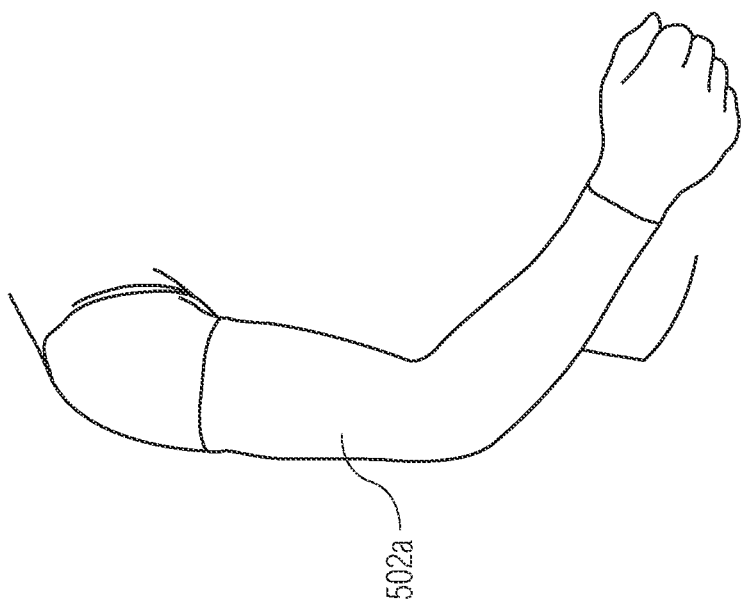
Figure 5F:
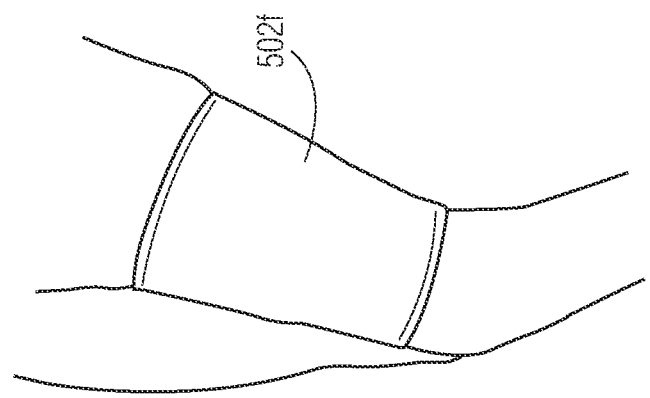
Figure 5E:
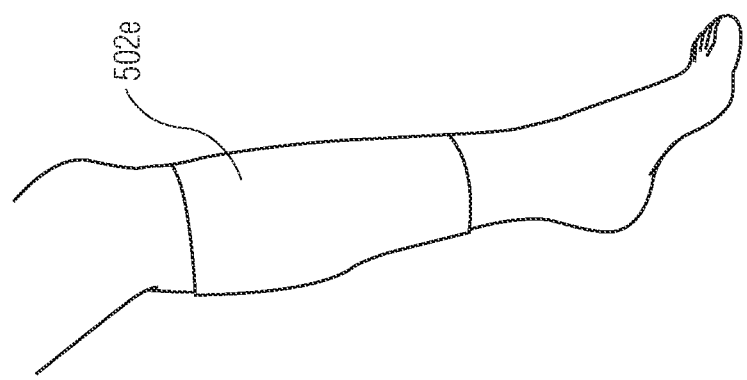
Figure 5D:
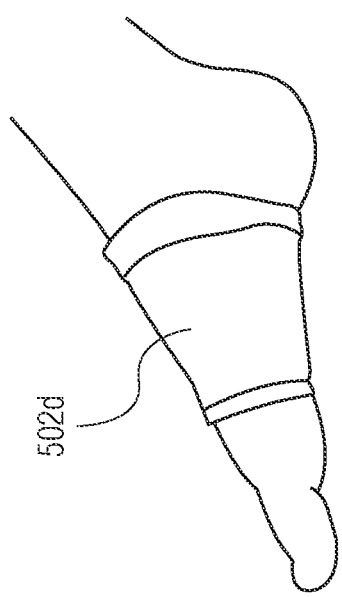
Figure 5I:
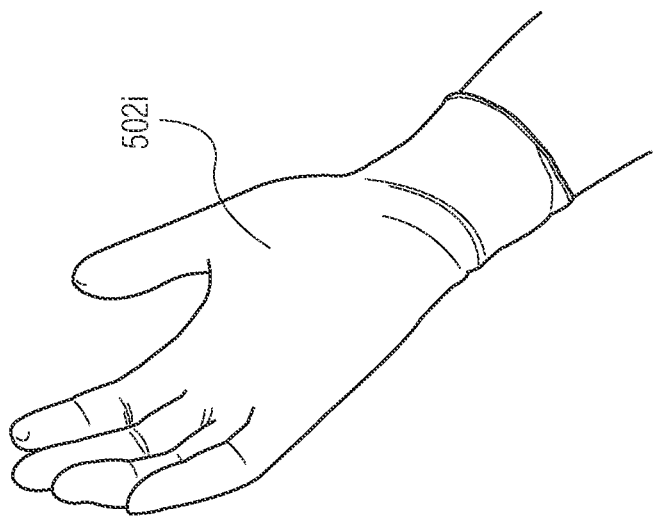
Figure 5H:
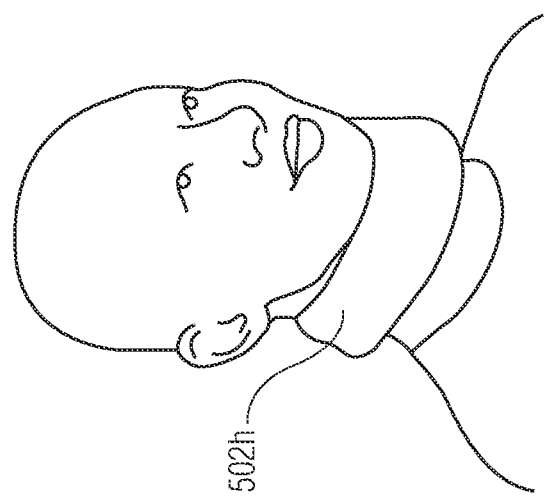
Figure 5G:
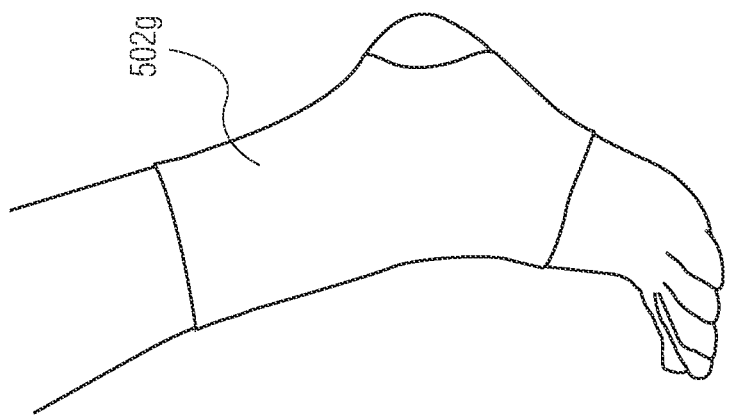
Figure 5K:
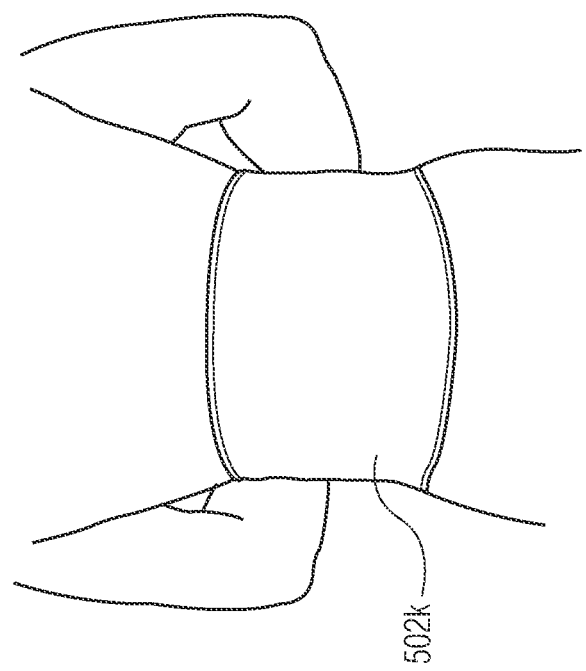
Figure 5J:
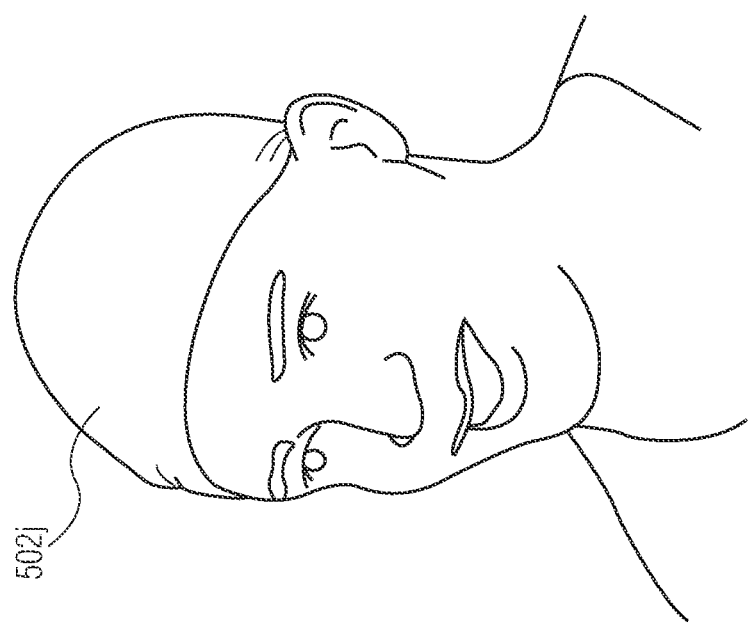

User device 102 shown in FIGS. 3A-3C and FIGS. 4A-4B, may take any of a number of shapes/configurations, depending on the treatment to be provided to the subject. For example, FIGS. 3A and 4A illustrate pain relief device 102 secured to the elbow of subject 100, where pain relief device 102 has the shape/configuration of a patch/medical pad. FIGS. 5A-5K illustrates various other exemplary pain relief devices 502a-502k which have the same (or substantially the same) functionality as pain relief device 102 described herein. That is, each of devices 502a-502k may include the elements shown in pain relief device 102 shown in FIG. 3C, or different elements within the scope of the invention. FIG. 5A illustrates pain relief device 502a having a sleeve shape for treating an elbow; FIG. 5B illustrates pain relief device 502b having a sleeve shape (such as a wrist guard or wrist wrap) for treating a wrist; FIG. 5C illustrates pain relief device 502c having a sleeve shape (such as a knee brace) for treating a knee; FIG. 5D illustrates pain relief device 502d having a sleeve shape for treating an foot (e.g., the arch of a foot); FIG. 5E illustrates pain relief device 502e having a sleeve shape for treating a calf; FIG. 5F illustrates pain relief device 502f having a sleeve shape for treating a upper leg (e.g., a thigh of a human subject); FIG. 5G illustrates pain relief device 502g having a sleeve shape for treating an ankle; FIG. 5H illustrates pain relief device 502h having a sleeve shape for treating a neck; FIG. 5I illustrates pain relief device 502i having a glove shape for treating a hand/wrist; FIG. 5J illustrates pain relief device 502j having a skull cap shape for treating a head; and FIG. 5K illustrates pain relief device 502k having a sleeve shape for treating a back/abdomen of a human subject. Of course, other shapes/configurations of pain relief devices are contemplated within the scope of the invention.

Figure 6:
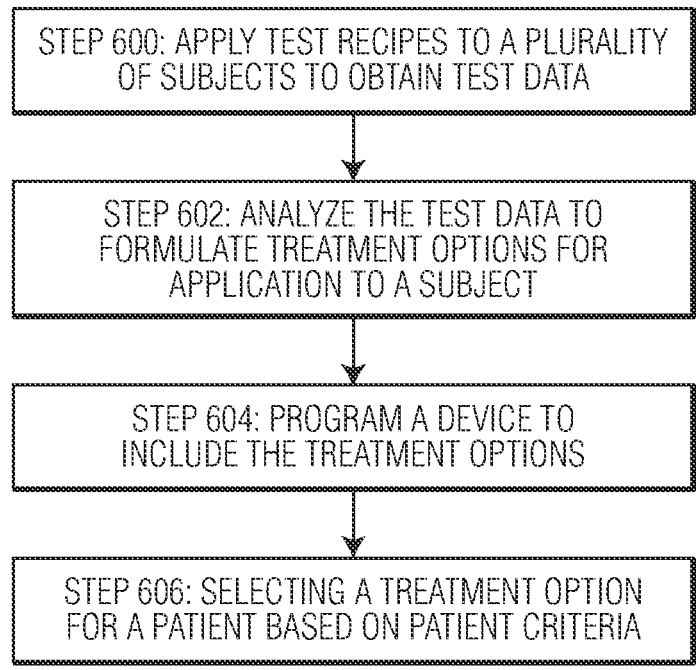
FIG. 6 is a flow diagram illustrating a method of determining a medical treatment for a subject in accordance with an exemplary embodiment of the invention.
Figure 7:
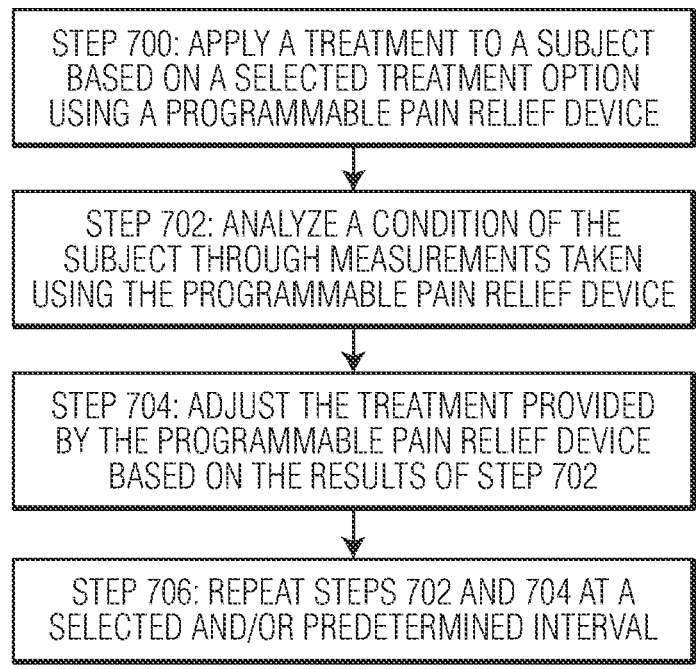
FIG. 7 is a flow diagram illustrating a method of applying a medical treatment to a subject in accordance with an exemplary embodiment of the invention.

FIGS. 6-7 are flow diagrams illustrating methods in accordance with the invention. As is understood by those skilled in the art, certain steps included in the flow diagrams may be omitted; certain additional steps may be added; and the order of the steps may be altered from the order illustrated.

Referring specifically to FIG. 6, a method of determining a medical treatment for a subject is provided. At Step 600, a plurality of test recipes are applied to a plurality of subjects (e.g., human subjects, other animal subjects, etc.) to obtain test data. At Step 602, the test data from the plurality of test recipes is analyzed to formulate treatment options for application to a subject. At Step 604, a device (e.g., a pain relief device such as pain relief devices 102 and 502a-502k illustrated and described herein) is programmed to include the treatment options. At Step 606, a treatment option is selected for a patient based on patient criteria. Examples of such patient criteria include at least one of an age of the subject, a gender of the subject, and feedback from the subject regarding prior treatment. Such patient criteria may be made accessible to an algorithm running on the pain relief device (e.g., using user device 300 in communication with the pain relief device).

Referring specifically to FIG. 7, a method of applying a medical treatment to a subject is provided. At Step 700, a treatment is applied to a subject based on a selected treatment option using a programmable pain relief device (e.g., pain relief device 102 including programmable device 102d). For example, the treatment option may have been selected by: a subject (e.g., a human patient); a medical professional on behalf of the patient; or a third party. In such an example, the pain relief device may have been initially configured with the selected treatment option. Alternatively, the subject (or the medical professional or the third party) may communicate with the pain relief device (e.g., using a user device, such as user device 300) to select the treatment option. At Step 702, a condition of the subject is analyzed through measurements taken using the programmable pain relief device. For example, referring to FIG. 3C, measurements may be taken using waveform analyzer 102d2 (e.g., receiving signals from monopolar transmitter 102c), where the measurements may be analyzed using controller 102d4 and/or memory 102d5. At Step 704, the treatment is adjusted by the programmable pain relief device based on the results of Step 704. That is, after measurements are taken (and analyzed at Step 704), it may be determined that the treatment applied in Step 700 may need to be adjusted. At Step 706, Steps 702-704 are repeated, as desired in the given application (e.g., at a selected interval, at a predetermined interval, etc.).

While aspects the invention have been described primarily in connection with certain examples, the invention is not limited to those examples. Providing a pain relief device including a monopolar transmitter (having a single electrical pole) for passing electrical signals to a subject has broad applicability beyond the examples described herein. Likewise, the use of a user device to communicate with the pain relief device (e.g., using bluetooth communication) to apply, or adjust, treatment options for a subject (e.g., a human patient) also has broad applicability beyond the examples described herein.

The invention is not limited to the embodiments described and exemplified above, but is capable of variation and modification within the scope of the appended claims.

What is claimed:

1. A method of treating a subject, the method comprising the steps of:
    (a) applying a body portion of a pain relief device to the subject, the body portion of the pain relief device configured to be in contact with the subject, the pain relief device including a monopolar transmitter including a single electrical pole for providing an electrical signal to the body portion for treatment of the subject, the monopolar transmitter being an antenna through which the electrical signal is provided, the monopolar transmitter being included as part of a monopolar transceiver, the monopolar transceiver measuring waveforms occurring on a surface of the subject; and (b) transmitting the electrical signal to the subject directly through the body portion using the monopolar transmitter; and (c) interacting the electrical signal transmitted directly through the body portion of the pain relief device by the monopolar transmitter with the subject to provide the treatment directly through an interface between the body portion of the pain relief device and the subject.

2. The method of claim 1, wherein a frequency of the electrical signal transmitted to the subject in step (b) is between 0.1 Hz and 20 Hz.

3. The method of claim 1, wherein a voltage of the electrical signal transmitted to the subject in step (b) is between 0.1 millivolts and 10 volts.

4. A method of applying a treatment to a subject, the method comprising the steps of:

(a) applying the treatment to the subject based on a selected treatment option via a programmable pain relief device, the programmable pain relief device including a body portion in contact with the subject, the programmable pain relief device including a monopolar transmitter including a single electrical pole for providing electrical signals to the body portion for the treatment of the subject, the monopolar transmitter being an antenna through which the electrical signals are provided, the monopolar transmitter being included as part of a monopolar transceiver, the monopolar transceiver measuring waveforms occurring on a surface of the subject, the treatment of the subject provided by the programmable pain relief device via the electrical signals transmitted directly through the body portion of the programmable pain relief device by the monopolar transmitter, the electrical signals interacting with the subject to provide the treatment directly through an interface between the body portion of the programmable pain relief device and the subject;

(b) analyzing a condition of the subject through measurements taken using the programmable pain relief device; and (c) adjusting the treatment provided by the programmable pain relief device based on results of step (b).

5. The method of claim 4 further comprising the step of:

(d) repeating steps (b) and (c) at a predetermined interval.

6. The method of claim 4, prior to step (a), the method further comprising the steps of: (d) applying test recipes to a plurality of subjects to obtain test data; (e) analyzing the test data to formulate treatment options for application to the subject; and (f) programming the programmable pain relief device to include the treatment options.

7. The method of claim 4, the selected treatment option being based on patient criteria of the subject.

8. The method of claim 7, wherein the patient criteria of the subject includes at least one of (i) an age of the subject, (ii) a gender of the subject, and (iii) feedback from the subject regarding prior treatment.

9. A method for treating a subject, the method comprising the steps of:

a. measuring naturally occurring waveforms on a surface of a body of a subject in response to applying a body portion of a pain relief device to the subject, the body portion of the pain relief device configured to be in contact with the subject, the pain relief device including a monopolar transmitter including a single electrical pole for providing electrical signals to the body portion for treatment of the subject, the monopolar transmitter being an antenna through which the electrical signals are provided, the monopolar transmitter being included as part of a monopolar transceiver, the monopolar transceiver measuring waveforms occurring on a surface of the subject, the treatment of the subject provided by the pain relief device via the electrical signals transmitted directly through the body portion of the pain relief device by the monopolar transmitter, the electrical signals interacting with the subject to provide the treatment directly through an interface between the body portion of the pain relief device and the subject;

b. analyzing data resulting from the measuring step; and c. applying the treatment to the subject using the pain relief device based on results of step (b).

10. The method of claim 9, wherein step (b) includes analyzing the data to determine an association between the data and a medical condition.

* * * * *